(12) United States Patent
Alonso-Alija et al.

(10) Patent No.: US 7,705,043 B2
(45) Date of Patent: Apr. 27, 2010

(54) SUBSTITUTED AMINODICARBOXYLIC ACID DERIVATIVES HAVING PHARMACEUTICAL PROPERTIES

(75) Inventors: Cristina Alonso-Alija, Haan (DE); Michael Harter, Leverkusen (DE); Michael Hahn, Langenfeld (DE); Josef Pernerstorfer, Wuppertal (DE); Stefan Weigand, Wuppertal (DE); Johannes-Peter Stasch, Solingen (DE); Frank Wunder, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 498 days.

(21) Appl. No.: 11/581,261

(22) Filed: Oct. 10, 2006

(65) Prior Publication Data

US 2007/0179139 A1    Aug. 2, 2007

Related U.S. Application Data

(63) Continuation of application No. 10/469,817, filed as application No. PCT/EP02/01891 on Feb. 22, 2002, now abandoned.

(30) Foreign Application Priority Data

Mar. 7, 2001    (DE) .................. 101 10 750

(51) Int. Cl.
*A61K 31/34*    (2006.01)
*C07D 333/02*    (2006.01)

(52) U.S. Cl. .............. 514/461; 549/29; 549/429; 544/242; 544/336; 546/329; 514/438; 514/357; 514/256

(58) Field of Classification Search ........... 549/429, 549/29; 544/242, 336; 546/329; 514/461, 514/438, 357, 256
See application file for complete search history.

(56) References Cited

U.S. PATENT DOCUMENTS 5,981,573 A * 11/1999 Iwasawa et al. ............ 514/466

\* cited by examiner

*Primary Examiner*—Rei-tsang Shiao
(74) *Attorney, Agent, or Firm*—Edwards Angell Palmer & Dodge LLP; Nicholas J. DiCeglie, Jr.; Barry Kramer

(57) ABSTRACT

The invention relates to compounds of formula (I) and their salts and stereoisomers

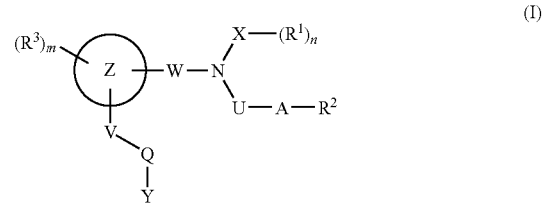

in which the variables are as defined in the description and claims, for producing medicaments used in the treatment of cardiovascular and other diseases. Such compounds, processes for preparing them, compositions containing them, and methods of using them are claimed.

11 Claims, No Drawings

SUBSTITUTED AMINODICARBOXYLIC ACID DERIVATIVES HAVING PHARMACEUTICAL PROPERTIES

The present invention relates to novel chemical compounds which stimulate soluble guanylate cyclase also via a novel mechanism of action which takes place without involvement of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory center. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in the neuronal signal transmission, and in disorders caused by an impairment of the aforementioned processes. Under pathophysiological conditions, the NO/cGMP system may be suppressed, which may lead for example to high blood pressure, platelet activation, increased cell proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmcol. 116 (1985), 307), isoliquiritigenin (Yu et al., Brit. J. Pharmacol. 114 (1995), 1587) and various substituted pyrazole derivatives (WO 98/16223, WO 98/16507 and WO 98/23619).

The stimulators of soluble guanylate cyclase known to date stimulate the enzyme either directly via the heme group (carbon monoxide, nitrogen monoxide or diphenyliodonium hexafluorophosphate) by interaction with the central iron of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating action of NO or CO (for example YC-1, Hoenicka et al., J. Mol. Med. (1999) 14; or the pyrazole derivatives described in WO 98/16223, WO 98/16507 and WO 98/23619).

The stimulating action of isoliquiritigenin and of fatty acids, such as, for example, arachidonic acid, prostaglandin endoperoxides and fatty acid hydroperoxides on soluble guanylate cyclase claimed in the literature could not be confirmed (cf., for example, Hoenicka et al., J. Mol. Med. 77 (1999), 14).

If the heme group is removed from soluble guanylate cyclase, the enzyme still has detectable catalytic basal activity, i.e. cGMP is still being formed. The residual catalytic basal activity of the heme-free enzyme cannot be stimulated by any of the known stimulators mentioned above.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, as a consequence of which the addition of protoporphyrin IX to soluble guanylate cyclase would be expected to result in the formation of a structure of the enzyme corresponding to heme-containing soluble guanylate cyclase stimulated by NO. This is also confirmed by the fact that the stimulating action of protoporphyrin IX is increased by the above-described NO-independent but heme-dependent stimulator YC-1 (Mülsch et al., Naunyn Schmiedebergs Arch. Pharmacol. 355, R47).

Thus, hitherto compounds capable of stimulating soluble guanylate cyclase independently of the heme group present in the enzyme have not been described.

It was an object of the present invention to provide medicaments for treating cardiovascular disorders or other disorders accessible to therapy by influencing the cGMP signal pathway in organisms.

The above object is achieved by using compounds for preparing medicaments capable of stimulating soluble guanylate cyclase even independently of NO and the heme group present in the enzyme.

Surprisingly, it has been found that there are compounds capable of stimulating soluble guanylate cyclase even independently of the heme group present in the enzyme. The biological activity of these stimulators is based on an entirely novel mechanism for stimulating soluble guanylate cyclase. In contrast to the above-described compounds, known from the prior art as stimulators of soluble guanylate cyclase, the compounds according to the invention are capable of stimulating both the heme-containing and the heme-free form of soluble guanylate cyclase. Thus, in the case of these novel stimulators, stimulation of the enzyme is effected via a heme-independent path, and this is also confirmed by the fact that firstly the novel stimulators do not have any synergistic action with NO at the heme-containing enzyme and that secondly the action of these novel stimulators cannot be blocked by the heme-dependent inhibitor of soluble guanylate cyclase, i.e. 1H-1,2,4-oxadiazole-(4,3a)-quinoxalin-1-one (ODQ).

This is a novel therapeutic approach for treating cardiovascular disorders and other disorders accessible to therapy by influencing the cGMP signal pathway in organisms.

EP-A-0 345 068 describes, inter alia, the aminoalkanecarboxylic acid (1) as an intermediate in the synthesis of GABA antagonists:

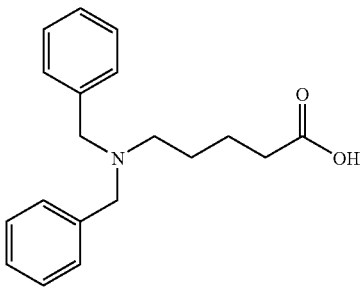

(1)

WO 93/00359 describes the aminoalkanecarboxylic acid (2) as an intermediate in peptide synthesis and its use as active compound for treating disorders of the central nervous system:

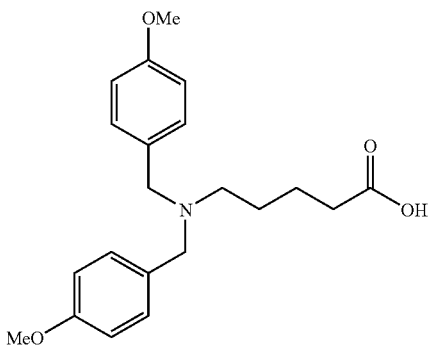

(2)

However, neither of these two publications describes that such aminoalkane-carboxylic acids may have a stimulating effect, independent of the heme group present in the enzyme, on soluble guanylate cyclase.

Substances having a structure similar to that of the compounds according to the invention are furthermore known from WO 01/19776, WO 01/19355, WO 01/19780 and WO 01/19778.

According to the present invention, the compounds used for stimulating, independently of the heme group present in the enzyme, soluble guanylate cyclase are aminoalkanecarboxylic acids of the formula (I):

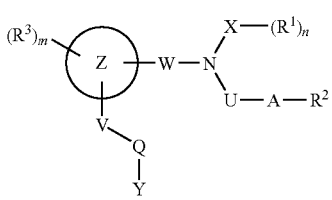

(I)

where

Z represents a phenyl ring which is fused with a saturated, partially unsaturated or aromatic carba- or heterocycle having up to 3 heteroatoms from the group consisting of S, N and/or O or with a partially unsaturated or aromatic heterocycle having 1 to 9 carbon atoms and up to 3 heteroatoms from the group consisting of S, N and/or O, V is missing or represents O, $NR^4$, $NR^4CONR^4$, $NR^4CO$, $NR^4SO_2$, COO, $CONR^4$ or $S(O)_o$, where
$R^4$ independently of any other radical $R^4$ optionally present represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms, o represents 0, 1 or 2, Q is missing or represents straight-chain or branched alkylene, straight-chain or branched alkenediyl or straight-chain or branched alkynediyl having in each case up to 12 carbon atoms, which radicals may in each case comprise one or more groups selected from the group consisting of O, $S(O)_p$, $NR^5$, CO, $NR^5SO_2$ or $CONR^5$ and which may be mono- or polysubstituted by halogen, hydroxyl or alkoxy having up to 4 carbon atoms, where optionally any two atoms of the above chain may be attached to one another forming a three- to eight-membered ring, where
$R_5$ represents hydrogen, straight-chain or branched alkyl having up to 8 carbon atoms or cycloalkyl having 3 to 8 carbon atoms which may be substituted by halogen or alkoxy having up to 4 carbon atoms, p represents 0, 1 or 2, Y represents hydrogen, $NR^8R^9$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N, where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 8 carbon atoms, straight-chain or branched cycloalkyl having 3 to 8 carbon atoms, halogen, hydroxyl, CN, $SR^6$, $NO_2$, $NR^8R^9$, $NR^7COR^{10}$, $NR^7CONR^7R^{10}$ or $CONR^{11}R^{12}$, where
$R^6$ represents hydrogen, straight-chain or branched alkyl having up to 8 carbon atoms, straight-chain or branched haloalkyl having up to 8 carbon atoms or cycloalkyl having 3 to 8 carbon atoms, $R^7$ independently of any other radical $R^7$ optionally present represents hydrogen, straight-chain or branched alkyl having up to 8 carbon atoms or cycloalkyl having 3 to 8 carbon atoms, $R^8$, $R^9$, $R^{11}$ and $R^{12}$ independently of one another represent hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{13}$, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms, or two substitutents selected from $R^8$ and $R^9$ or $R^{11}$ and $R^{12}$ may be attached to one another forming a five- or six-membered ring which may contain O or N, where R$^{13}$ represents straight-chain or branched alkyl having up to 4 carbon atoms or aryl having 6 to 10 carbon atoms, where the aryl radical for its part may be mono- or polysubstituted by halogen, CN, NO$_2$, alkyl, alkoxy, haloalkyl or haloalkoxy having up to 6 carbon atoms, R$^{10}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, NO$_2$, NH$_2$, NHCOR$^7$, alkyl, alkoxy, haloalkyl or haloalkoxy having up to 6 carbon atoms;

and/or the cyclic radicals may in each case be mono- to trisubstituted by aryl having 6 to 10 carbon atoms, a saturated carbocycle having 6 to 10 carbon atoms, an aromatic or saturated heterocycle having 1 to 9 carbon atoms and up to 3 heteroatoms from the group consisting of S, N and O, which may also be attached via N, which may be attached directly or via a group selected from the group consisting of O, S, SO, SO$_2$, NR$^7$, SO$_2$NR$^7$, CONR$^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched haloalkyl, straight-chain or branched haloalkoxy, carbonylalkyl or straight-chain or branched alkenyl having in each case up to 6 carbon atoms, halogen, SR$^6$, CN, NO$_2$, NR$^8$R$^9$, CONR$^{15}$R$^{16}$ or NR$^{14}$COR$^{17}$, where R$^{14}$ represents hydrogen, straight-chain or branched alkyl having up to 8 carbon atoms or cycloalkyl having 3 to 8 carbon atoms, R$^{15}$, R$^{16}$ independently of one another represent hydrogen, straight-chain or branched alkyl having up to 8 carbon atoms, cycloalkyl having 3 to 8 carbon atoms, aryl having 6 to 10 carbon atoms or a radical of the formula SO$_2$R$^{18}$, where the aryl radical for its part may be mono- or polysubstituted by halogen, hydroxyl, CN, NO$_2$, NH$_2$, NHCOR$^7$, alkyl, alkoxy, haloalkyl or haloalkoxy having up to 6 carbon atoms, where R$^{18}$ represents straight-chain or branched alkyl having up to 4 carbon atoms or aryl having 6 to 10 carbon atoms, where the aryl radical for its part may be mono- or polysubstituted by halogen, hydroxyl, CN, NO$_2$, NH$_2$, NHCOR$^7$, alkyl, alkoxy, haloalkyl or haloalkoxy having up to 6 carbon atoms, and R$^{17}$ independently of one another represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, NO$_2$, NH$_2$, NHCOR$^7$, alkyl, alkoxy, haloalkyl or haloalkoxy having up to 6 carbon atoms;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, R$^3$ represents hydrogen, halogen, straight-chain or branched alkyl which may optionally carry one or more substituents from the group consisting of C$_{1-6}$-alkoxy, NR$^{19}$R$^{20}$ and cycloalkyl having 3 to 8 carbon atoms, straight-chain or branched haloalkyl, straight-chain or branched alkoxy, or alkoxycarbonyl having in each case up to 4 carbon atoms, CN, NO$_2$, NR$^{19}$R$^{20}$, SR$^{17}$, SO$_2$R$^{17}$, cycloalkyl having 3 to 8 carbon atoms, haloalkoxy, haloalkoxy having up to 6 carbon atoms, cycloalkoxy having up to 14 carbon atoms, CONH$_2$, CONR$^{17}$R$^{17}$, SO$_2$NH$_2$, SO$_2$NR$^{17}$R$^{17}$, alkoxyalkoxy having up to 12 carbon atoms, NHCOOR$^{17}$, NHCOR$^{17}$, NHSO$_2$R$^{17}$, NHCONH$_2$, OCONR$^{17}$R$^{17}$, OSO$_2$R$^{17}$, C$_{2-12}$-alkenyl or C$_{2-12}$-alkynyl, where R$^{19}$ and R$^{20}$ independently of one another represent hydrogen, straight-chain or branched alkyl having up to 4 carbon atoms or cycloalkyl having 3 to 8 carbon atoms, m represents an integer from 1 to 4, W represents straight-chain or branched alkylene having up to 6 carbon atoms or straight-chain or branched alkenediyl having up to 6 carbon atoms which may in each case contain a group selected from the group consisting of O, S(O)$_q$, NR$^{21}$, CO or CONR$^{21}$, or represents CO, NHCO or OCO, where q represents 0, 1 or 2, R$^{21}$ represents hydrogen, straight-chain or branched alkyl having up to 8 carbon atoms or cycloalkyl having 3 to 8 carbon atoms, U represents straight-chain or branched alkyl having up to 4 carbon atoms, A represents aryl having 6 to 10 carbon atoms or an aromatic heterocycle having 1 to 9 carbon atoms and up to 3 heteroatoms from the group consisting of S, N and O, which may optionally be mono- to trisubstituted by halogen, straight-chain or branched alkyl, straight-chain or branched haloalkyl, straight-chain or branched alkoxy, haloalkoxy or alkoxycarbonyl having up to 4 carbon atoms, CN, NO$_2$ or NR$^{22}$R$^{23}$, where R$^{22}$ and R$^{23}$ in each case independently of one another represent hydrogen, straight-chain or branched alkyl having up to 8 carbon atoms or cycloalkyl having 3 to 8 carbon atoms, carbonylalkyl or sulfonylalkyl, R$_2$ represents tetrazolyl, COOR$^{24}$ or CONR$^{25}$R$^{26}$, where R$^{24}$ [lacuna] hydrogen, alkyl having 1 to 8 carbon atoms or cycloalkyl having 3 to 8 carbon atoms R$^{25}$ and R$^{26}$ in each case independently of one another represent hydrogen, straight-chain or branched alkyl having up to 8 carbon atoms, cycloalkyl having 3 to 8 carbon atoms or a radical of the formula SO$_2$R$^{27}$, or R$^{25}$ and R$^{26}$ together form a five- or six-membered ring which may contain N or O, where
R²⁷ represents straight-chain or branched alkyl having up to 4 carbon atoms or aryl having 6 to 10 carbon atoms, where the aryl radical for its part may be mono- or polysubstituted by halogen, CN, NO₂, alkyl, alkoxy, haloalkyl or haloalkoxy having up to 6 carbon atoms, X represents straight-chain or branched alkylene having up to 12 carbon atoms or straight-chain or branched alkenediyl having up to 12 carbon atoms, which may in each case contain one to three groups selected from the group consisting of O, S(O)ᵣ, NR²⁸, CO or CONR²⁹, aryl and aryloxy having 6 to 10 carbon atoms, where the aryl radical for its part may be mono- or polysubstituted by halogen, CN, NO₂, alkyl, alkoxy, haloalkyl or haloalkoxy having up to 6 carbon atoms, where optionally any two atoms of the abovementioned chains are attached to one another via an alkyl chain forming a three- to eight-membered ring,
where
r represents 0, 1 or 2,
R²⁸ represents hydrogen, alkyl having 1 to 8 carbon atoms or cycloalkyl having 3 to 8 carbon atoms,
R²⁹ represents hydrogen, straight-chain or branched alkyl having up to 8 carbon atoms or cycloalkyl having 3 to 8 carbon atoms,
n represents 1 or 2;
R¹ represents tetrazolyl, COOR³⁰ or CONR³¹R³²,
where
R³⁰ [lacuna] hydrogen, alkyl having 1 to 8 carbon atoms or cycloalkyl having 3 to 8 carbon atoms
R³¹ and R³² in each case independently of one another represent hydrogen, straight-chain or branched alkyl having up to 8 carbon atoms, cycloalkyl having 3 to 8 carbon atoms or a radical of the formula SO₂R³³,
where
R³³ represents straight-chain or branched alkyl having up to 4 carbon atoms or aryl having 6 to 10 carbon atoms,
where the aryl radical for its part may be mono- or polysubstituted by halogen, CN, NO₂, alkyl, alkoxy, haloalkyl or haloalkoxy having up to 6 carbon atoms, and their stereoisomers and salts.

Here, preference is given to compounds of the formula (I) where

Z represents a cyclic radical from the group consisting of

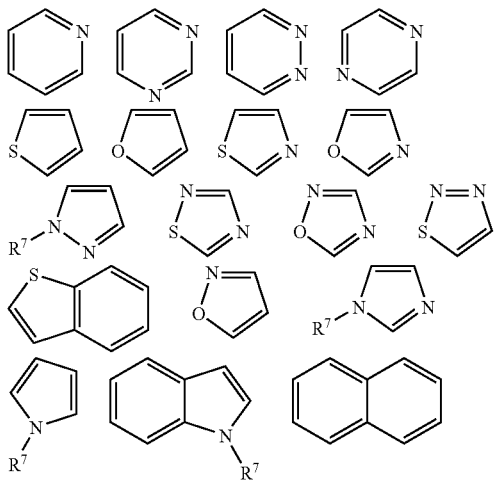

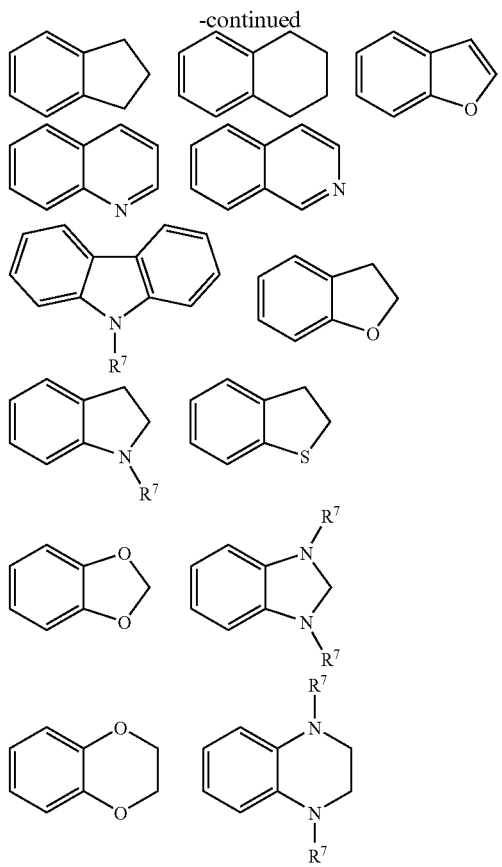

where the radicals V and W may be attached to any carbon ring atom or any nitrogen ring atom optionally present, selected;

V is missing or represents O, NR⁴, NR⁴CONR⁴, NR⁴CO, NR⁴SO₂, COO, CONR⁴ or S(O)ₒ,
where
R⁴ independently of any other radical R⁴ optionally present represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o represents 0, 1 or 2, Q is missing or represents straight-chain or branched alkylene, straight-chain or branched alkenediyl or straight-chain or branched alkynediyl having in each case up to 12 carbon atoms, which radicals may in each case comprise one or more groups selected from the group consisting of O, S(O)ₚ, NR⁵, CO, NR⁵SO₂ or CONR⁵ and which may be mono- or polysubstituted by halogen, hydroxyl or alkoxy having up to 4 carbon atoms, where optionally any two atoms of the above chain may be attached to one another forming a three- to eight-membered ring,
where
R₅ represents hydrogen, straight-chain or branched alkyl having up to 8 carbon atoms or cycloalkyl having 3 to 8 carbon atoms which may be substituted by halogen or alkoxy having up to 4 carbon atoms,
p represents 0, 1 or 2, Y represents hydrogen, $NR^8R^9$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N, where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 8 carbon atoms, straight-chain or branched cycloalkyl having 3 to 8 carbon atoms, halogen, hydroxyl, CN, $SR^6$, $NO_2$, $NR^8R^9$, $NR^7COR^{10}$, $NR^7CONR^7R^{10}$ or $CONR^{11}R^{12}$, where $R^6$ represents hydrogen, straight-chain or branched alkyl having up to 8 carbon atoms, straight-chain or branched haloalkyl having up to 8 carbon atoms or cycloalkyl having 3 to 8 carbon atoms, $R^7$ independently of any other radical $R^7$ optionally present represents hydrogen, straight-chain or branched alkyl having up to 8 carbon atoms or cycloalkyl having 3 to 8 carbon atoms, $R^8, R^9, R^{11}$ and $R^{12}$ independently of one another represent hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{13}$, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms, or two substituents selected from $R^8$ and $R^9$ or $R^{11}$ and $R^{12}$ may be attached to one another forming a five- or six-membered ring which may contain O or N, where $R^{13}$ represents straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, haloalkyl or haloalkoxy having up to 6 carbon atoms, $R^{10}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^7$, alkyl, alkoxy, haloalkyl or haloalkoxy having up to 6 carbon atoms;

and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N, which may be attached directly or via a group selected from the group consisting of O, S, SO, $SO_2$, $NR^7$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched haloalkyl, straight-chain or branched haloalkoxy, carbonylalkyl or straight-chain or branched alkenyl having in each case up to 6 carbon atoms, halogen, $SR^6$, CN, $NO_2$, $NR^8R^9$, $CONR^{15}R^{16}$ or $NR^{14}COR^{17}$, where $R^{14}$ represents hydrogen, straight-chain or branched alkyl having up to 8 carbon atoms or cycloalkyl having 3 to 8 carbon atoms, $R^{15}, R^{16}$ independently of one another represent hydrogen, straight-chain or branched alkyl having up to 8 carbon atoms, cycloalkyl having 3 to 8 carbon atoms or a radical of the formula $SO_2R^{18}$, where $R^{18}$ represents straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, haloalkyl or haloalkoxy having up to 6 carbon atoms, and $R^{17}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, CN, $NO_2$, alkyl, alkoxy, haloalkyl or haloalkoxy having up to 6 carbon atoms;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ represents hydrogen, halogen, straight-chain or branched alkyl, straight-chain or branched haloalkyl or straight-chain or branched alkoxy having in each case up to 4 carbon atoms, m represents an integer from 1 to 4, W represents straight-chain or branched alkylene or straight-chain or branched alkenediyl having in each case up to 4 carbon atoms, U represents —$CH_2$—, A represents phenyl or an aromatic heterocycle having 1 to 9 carbon atoms and up to 3 heteroatoms from the group consisting of S, N and O, which may optionally be mono- to trisubstituted by halogen, straight-chain or branched alkyl, straight-chain or branched haloalkyl or straight-chain or branched alkoxy having up to 4 carbon atoms, $R^2$ represents $COOR^{24}$, where $R^{24}$ represents hydrogen or straight-chain or branched alkyl having up to 6 carbon atoms, X represents straight-chain or branched alkylene having up to 8 carbon atoms or straight-chain or branched alkenediyl having up to 8 carbon atoms which may in each case contain one to three groups selected from the group consisting of phenyl, phenyloxy, O, CO and $CONR^{29}$, where $R^{29}$ represents hydrogen, straight-chain or branched alkyl having up to 6 carbon atoms or cycloalkyl having 3 to 6 carbon atoms, n represents 1 or 2;

$R^1$ represents $COOR^{30}$, where $R^{30}$ represents hydrogen or straight-chain or branched alkyl having up to 6 carbon atoms.

Particular preference is given to compounds of the formula (I)

where

Z represents a cyclic radical from the group consisting of

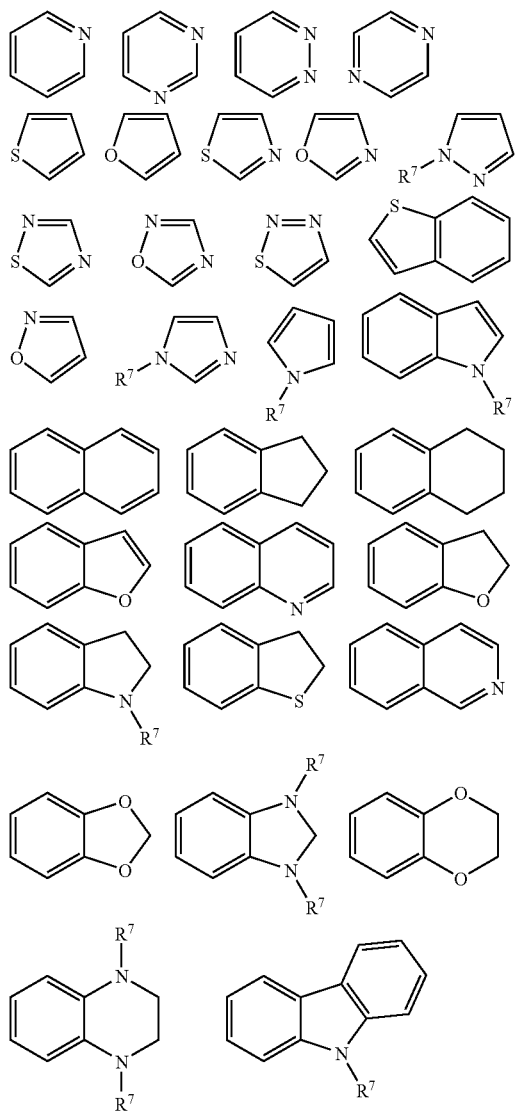

where the radicals V and W may be attached to any carbon ring atom or any nitrogen ring atom optionally present, selected;

V is missing or represents O, S or $NR^4$, where $R^4$ represents hydrogen or methyl, Q is missing or represents straight-chain or branched alkylene having up to 9 carbon atoms or straight-chain or branched alkenediyl or straight-chain or branched alkynediyl having up to 4 carbon atoms which may be monosubstituted by halogen, Y represents H, $NR^8R^9$, cyclohexyl, phenyl, naphtyl or a heterocycle selected from the group consisting of

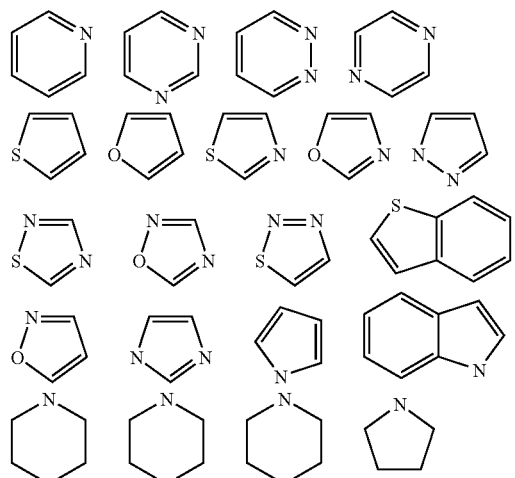

which may also be attached via N, where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$, where $R^6$ represents hydrogen, straight-chain or branched alkyl having up to 8 carbon atoms, or straight-chain or branched haloalkyl having up to 4 carbon atoms, $R^7$ represents hydrogen, or straight-chain or branched alkyl having up to 4 carbon atoms, $R^8, R^9, R^{11}$ and $R^{12}$ independently of one another represent hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents selected from $R^8$ and $R^9$ or $R^{11}$ and $R^{12}$ may be attached to one another forming a five- or six-membered ring which may be interrupted by O or N, $R^{10}$ represents hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

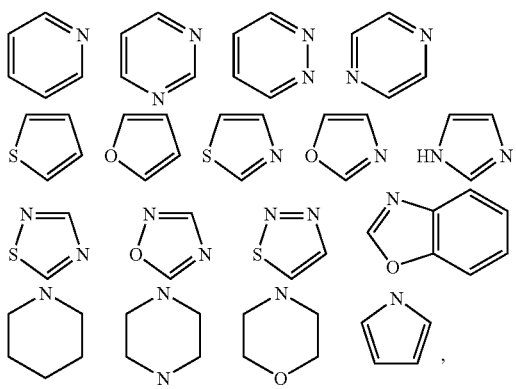

which may be attached directly or via a group selected from the group consisting of O, S, SO, $SO_2$, $NR^4$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched haloalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$, where $R^{14}$ represents hydrogen, straight-chain or branched alkyl having up to 8 carbon atoms or cycloalkyl having 3 to 8 carbon atoms, and $R^{17}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms selected from the group consisting of S, N and O, $R^3$ represents hydrogen, methyl or fluorine, m represents an integer from 1 to 4, W represents $CH_2$, $—CH_2CH_2—$, $CH_2CH_2CH_2$, $CH=CHCH_2$, U represents $—CH_2—$, A represents phenyl, pyridyl, thienyl or thiazolyl which may optionally be mono- to trisubstituted by methyl, ethyl, n-propyl, i-propyl, n-butyl, i-butyl, s-butyl, t-butyl, $CF_3$, methoxy, ethoxy, F, Cl, Br, $R^2$ represents $COOR^{24}$, where $R^{24}$ represents hydrogen or straight-chain or branched alkyl having up to 4 carbon atoms, X represents straight-chain or branched alkylene having up to 8 carbon atoms or straight-chain or branched alkenediyl having up to 8 carbon atoms which may in each case contain one to three groups from the group consisting of phenyl, phenyloxy, O, CO and $CONR^{30}$, where $R^{30}$ represents hydrogen, straight-chain or branched alkyl having up to 6 carbon atoms or cycloalkyl having 3 to 6 carbon atoms, n represents 1 or 2;

$R^1$ represents $COOR^{35}$, where $R^{35}$ represents hydrogen or straight-chain or branched alkyl having up to 6 carbon atoms.

Here, very particular preference is given to compounds of the formula (I)

where

Z represents a cyclic radical from the group consisting of

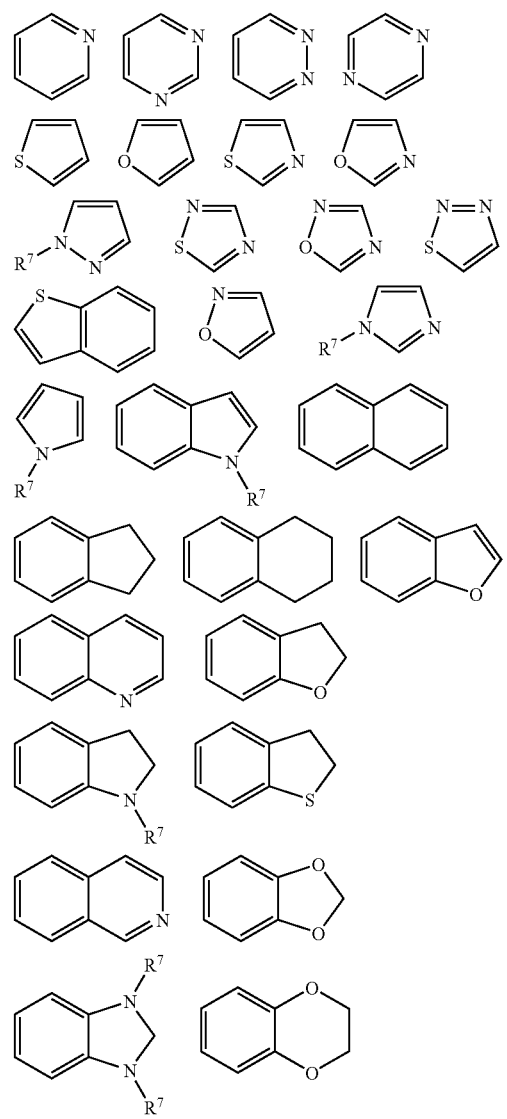

-continued

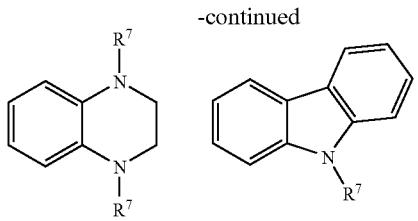

where the radicals V and W may be attached to any carbon ring atom or any nitrogen ring atom optionally present, selected;

V represents O,

Q represents straight-chain or branched alkylene having up to 9 carbon atoms or straight-chain or branched alkenediyl or straight-chain or branched alkynediyl having up to 4 carbon atoms which may be monosubstituted by halogen, Y represents H, cyclohexyl, phenyl or a heterocycle from the group consisting of

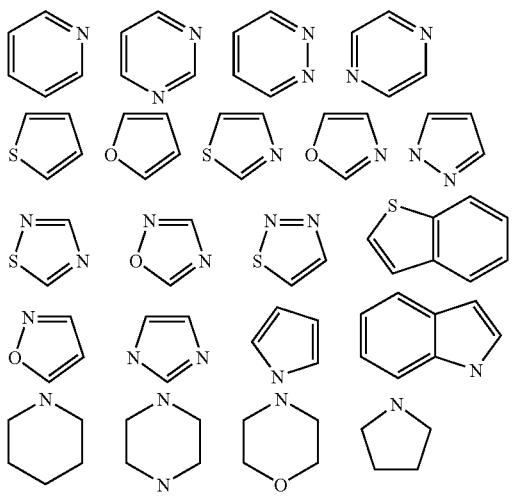

where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$, where $R^6$ represents hydrogen, straight-chain or branched alkyl having up to 4 carbon atoms, or straight-chain or branched haloalkyl having up to 4 carbon atoms, $R^7$ represents hydrogen, or straight-chain or branched alkyl having up to 4 carbon atoms, $R^8, R^9, R^{11}$ and $R^{12}$ independently of one another represent hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents selected from $R^8$ and $R^9$ or $R^{11}$ and $R^{12}$ may be attached to one another forming a five- or six-membered ring which may be interrupted by O or N, $R^{10}$ represents hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

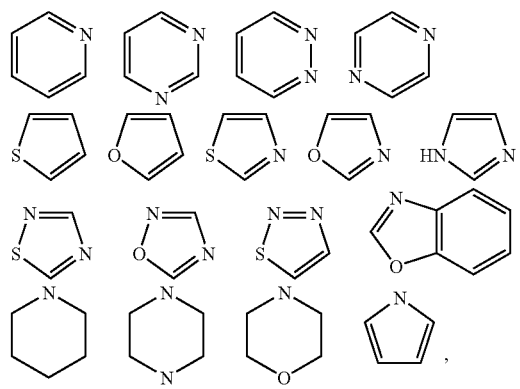

which may be attached directly or via a group selected from the group consisting of O, S, SO, $SO_2$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched haloalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$, where $R^{14}$ represents hydrogen, straight-chain or branched alkyl having up to 6 carbon atoms or cycloalkyl having 3 to 6 carbon atoms, and $R^{17}$ represents hydrogen, straight-chain or branched alkyl having up to 6 carbon atoms, straight-chain or branched alkenyl having up to 6 carbon atoms, aryl having 6 to 10 carbon atoms, an aromatic heterocycle having 1 to 9 carbon atoms and up to 3 heteroatoms from the group consisting of S, N and O or cycloalkyl having 3 to 6 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms selected from the group consisting of S, N and O, $R^3$ represents hydrogen, methyl or fluorine, m represents an integer from 1 to 2, W represents $CH_2$, or $-CH_2CH_2-$, U represents $-CH_2-$, A represents phenyl, which may optionally be mono- to trisubstituted by methyl, ethyl, n-propyl, i-propyl, n-butyl, i-butyl, s-butyl, t-butyl, $CF_3$, methoxy, ethoxy, F, Cl, Br, $R^2$ represents $COOR^{24}$, where $R^{24}$ represents hydrogen or straight-chain or branched alkyl having up to 4 carbon atoms, X represents straight-chain or branched alkylene having up to 6 carbon atoms or straight-chain or branched alkenediyl having up to 6 carbon atoms which may in each case contain one to three groups from the group consisting of phenyloxy, O, CO and $CONR^{30}$, where $R^{30}$ represents hydrogen, straight-chain or branched alkyl having up to 6 carbon atoms or cycloalkyl having 3 to 6 carbon atoms, n represents 1 or 2;

$R^1$ represents $COOR^{35}$, where $R^{35}$ represents hydrogen or straight-chain or branched alkyl having up to 4 carbon atoms.

Particular preference according to the invention is given to compounds of the formula (I) in which $R^1$ and $R^2$ are each COOH.

Very particular preference according to the present invention is given to compounds in which Z represents a cyclic radical from the group consisting of -continued where the radicals V and W may be attached to any carbon ring atom or any nitrogen ring atom optionally present, selected;

V represents O,

Q represents $CH_2$,

Y represents phenyl which is substituted by a radical selected from the group consisting of 2-phenylethyl, cyclohexyl, 4-chlorophenyl, 4-methoxyphenyl, 4-trifluoromethylphenyl, 4-cyanophenyl, 4-chlorophenoxy, 4-methoxyphenoxy, 4-trifluoromethylphenoxy, 4-cyanophenoxy, 4-methylphenyl, $R^3$ represents hydrogen, methyl or fluorine, m represents an integer from 1 to 2, W represents $-CH_2CH_2-$, U represents $-CH_2-$, A represents phenyl, $R^2$ represents COOH, where $R^2$ is located in the 4-position to the radical U, X represents $(CH_2)_4$, $R^1$ represents COOH.

Very particular preference according to the present invention is also given to compounds in which Z represents a cyclic radical from the group consisting of

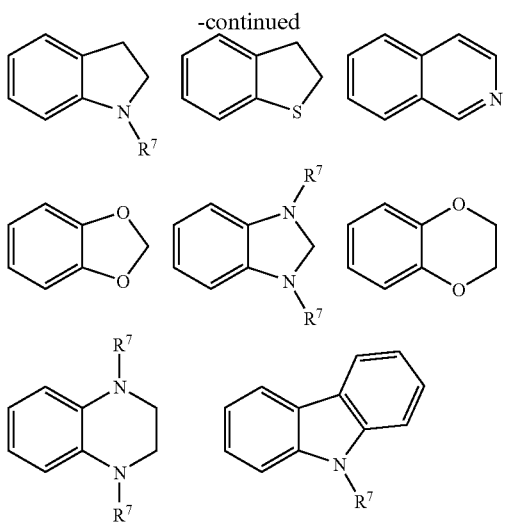

where the radicals V and W may be attached to any carbon ring atom or any nitrogen ring atom optionally present, selected;

V is missing,

Q represents CH$_2$O which is attached via its carbon atom to Z,

Y represents phenyl which is substituted by a radical selected from the group consisting of 2-phenylethyl, cyclohexyl, 4-chlorophenyl, 4-methoxyphenyl, 4-trifluoromethylphenyl, 4-cyanophenyl, 4-chlorophenoxy, 4-methoxyphenoxy, 4-trifluoromethylphenoxy, 4-cyanophenoxy, 4-methylphenyl, 4-tert-butylphenyl, 4-carboxyphenyl, 4-fluorophenyl, 3-methoxyphenyl, 2,4-dichlorophenyl, R$^3$ represents hydrogen, methyl or fluorine, m represents an integer from 1 to 2, W represents —CH$_2$CH$_2$—, U represents —CH$_2$—, A represents phenyl, R$^2$ represents COOH where R$^2$ is located in the 4-position to the radical U, X represents (CH$_2$)$_4$, R$^1$ represents COOH.

The compounds according to the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers), or not like image and mirror image (diastereomers). The invention relates both to the enantiomers or diastereomers and to their respective mixtures. The racemic forms, like the diastereomers, can be separated into the stereoisomerically uniform components in a known manner, for example by optical resolution or chromatographic separation. The double bonds present in the compounds according to the invention can be in the cis or trans configuration (Z or E form).

For the purposes of the present invention, the substituents are, unless defined otherwise, generally as defined below:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkylene generally represents a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodeylene and eicosylene.

Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkynyl generally represents a straight-chain or branched hydrocarbon radical having 2 to 20 carbon atoms and one or more, preferably one or two, triple bonds. Examples which may be mentioned are ethynyl, 2-butynyl, 2-pentynyl and 2-hexynyl.

Alkenediyl generally represents a straight-chain or branched hydrocarbon bridge having 2 to 20 carbon atoms and one or more, preferably one or two, double bonds. Examples which may be mentioned are ethene-1,2-diyl, propene-1,3-diyl, propene-1,2-diyl, 1-butene-1,4-diyl, 1-butene-1,3-diyl, 1-butene-1,2-diyl, 2-butene-1,4-diyl, 2-butene-1,3-diyl, 2-butene-2,3-diyl.

Alkynediyl generally represents a straight-chain or branched hydrocarbon bridge having 2 to 20 carbon atoms and one or more, preferably one or two, triple bonds. Examples which may be mentioned are ethyne-1,2-diyl, propyne-1,3-diyl, 1-butyne-1,4-diyl, 1-butyne-1,3-diyl, 2-butene-1,4-diyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms. Alkoxycarbonyl may be represented, for example, by the formula

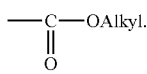

Here, alkyl generally represents a straight-chain or branched hydrocarbon radical having 1 to 13 carbon atoms. The following alkoxycarbonyl radicals may be mentioned by way of example: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Cyclopentyl, cyclohexyl, cycloheptyl and cyclooctyl may be mentioned by way of example.

Cycloalkoxy, for the purposes of the invention, represents an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen, for the purposes of the invention, represents fluorine, chlorine, bromine and iodine.

Heterocycle, for the purposes of the invention, generally represents a saturated, unsaturated or aromatic 3- to 10-membered, for example 5- or 6-membered, heterocycle which may contain up to 3 heteroatoms from the group consisting of S, N and O and which may, if a nitrogen atom is present, also be attached via this nitrogen atom. Examples which may be mentioned are: oxadiazolyl, thiadiazolyl, pyrazolyl, pyridyl, pyrimdinyl, pyridazinyl, pyrazinyl, thienyl, furyl, pyrrolyl, pyrrolidinyl, piperazinyl, tetrahydropyranyl, tetrahydrofuranyl, 1,2,3 triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") denotes an aromatic heterocyclic radical.

In the structures of heterocycles shown in the present application, in each case only one bond to the adjacent group is indicated, for example in the case of the heterocycle structures possible for Y the bond to the unit Q. However, independently thereof, these heterocycle structures may carry further substituents as indicated.

The present invention furthermore relates to a process for preparing the compounds of the formula (I), characterized in that

[A] compounds of the formula (II)

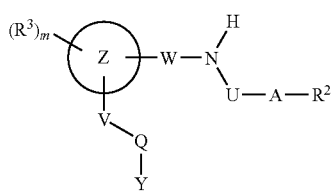

are reacted with compounds of the formula (III)

 (III)

where

Z, $R^1$, $R^2$, $R^3$, V, Q, Y, W, X, U, A and m are as defined above,

E represents either a leaving group which is substituted in the presence of a base or an optionally activated hydroxyl function;

or

[B] compounds of the formula (IV)

are reacted with compounds of the formula (V)

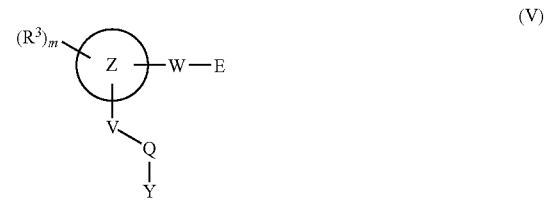

where

Z, $R^1$, $R^2$, $R^3$, V, Q, Y, W, X, U, A and m are as defined above,

E represents either a leaving group which is substituted in the presence of a base or an optionally activated hydroxyl function;

or

[C] compounds of the formula (VI)

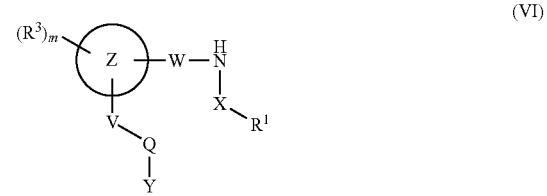

are reacted with compounds of the formula (VII)

 (VII)

where

Z, $R^1$, $R^2$, $R^3$, V, Q, Y, W, X, U, A and m are as defined above,

E represents either a leaving group which is substituted in the presence of a base or an optionally activated hydroxyl function;

or

[D] compounds of the formula (VIII)

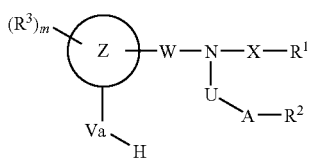

(VIII)

where
Va represents O or S and
Z, $R^1$, $R^2$, $R^3$, Y, Q, W, U, A, X and m are as defined above,
are reacted with compounds of the formula (IX)

(IX)

where
Q, Y are as defined above,
E represents either a leaving group which is substituted in the presence of a base or an optionally activated hydroxyl function;

or
[E] compounds of the formula (X)

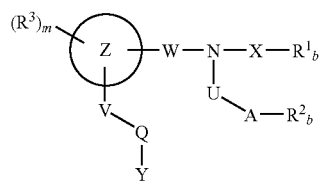

(X)

where
Z, $R^3$, V, Q, Y, W, X, U, A and m are as defined above,
$R^1_b$ and $R^2_b$ each independently of one another represent CN or COOAlk, where Alk represents a straight-chain or branched alkyl radical having up to 6 carbon atoms,
are converted with aqueous solutions of strong acids or strong bases into the corresponding free carboxylic acids.

or
[F] compounds of the formula (XI)

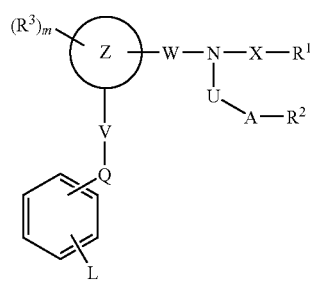

(XI)

where
Z, $R^1$, $R^2$, $R^3$, V, Q, X, W, U, A and m are as defined above,
L represents Br, I or the group $CF_3SO_2$—O, are reacted with compounds of the formula (XII)

M-Z'  (XII)

where
M represents an aryl or heteroaryl radical, a straight-chain or branched alkyl, alkenyl or alkynyl radical or cycloalkyl radical or represents an arylalkyl, an arylalkenyl or an arylalkynyl radical,
Z' represents the groupings —$B(OH)_2$, —CH≡CH, —CH=$CH_2$ or —$Sn(nBu)_3$
in the presence of a palladium compound, if appropriate additionally in the presence of a reducing agent and further additives and in the presence of a base;

or
[G] compounds of the formula (XIII)

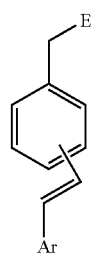

(XIII)

where
Ar represents an aryl or heteroaryl radical,
E represents a leaving group which is substituted in the presence of a base.
are reacted according to process D with compounds of the formula (VIII) and the resulting compounds of the formula (XIV)

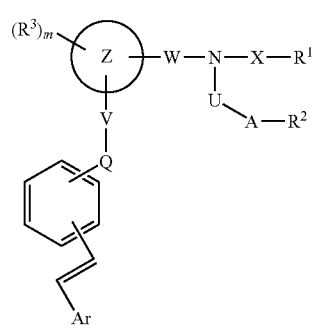

(XIV)

are hydrogenated with hydrogen in the presence of a catalyst.

The processes according to the invention for preparing compounds of the formula (I) are illustrated below using exemplary, non-limiting embodiments:

Example for the Reaction Sequence According to Process A/E:
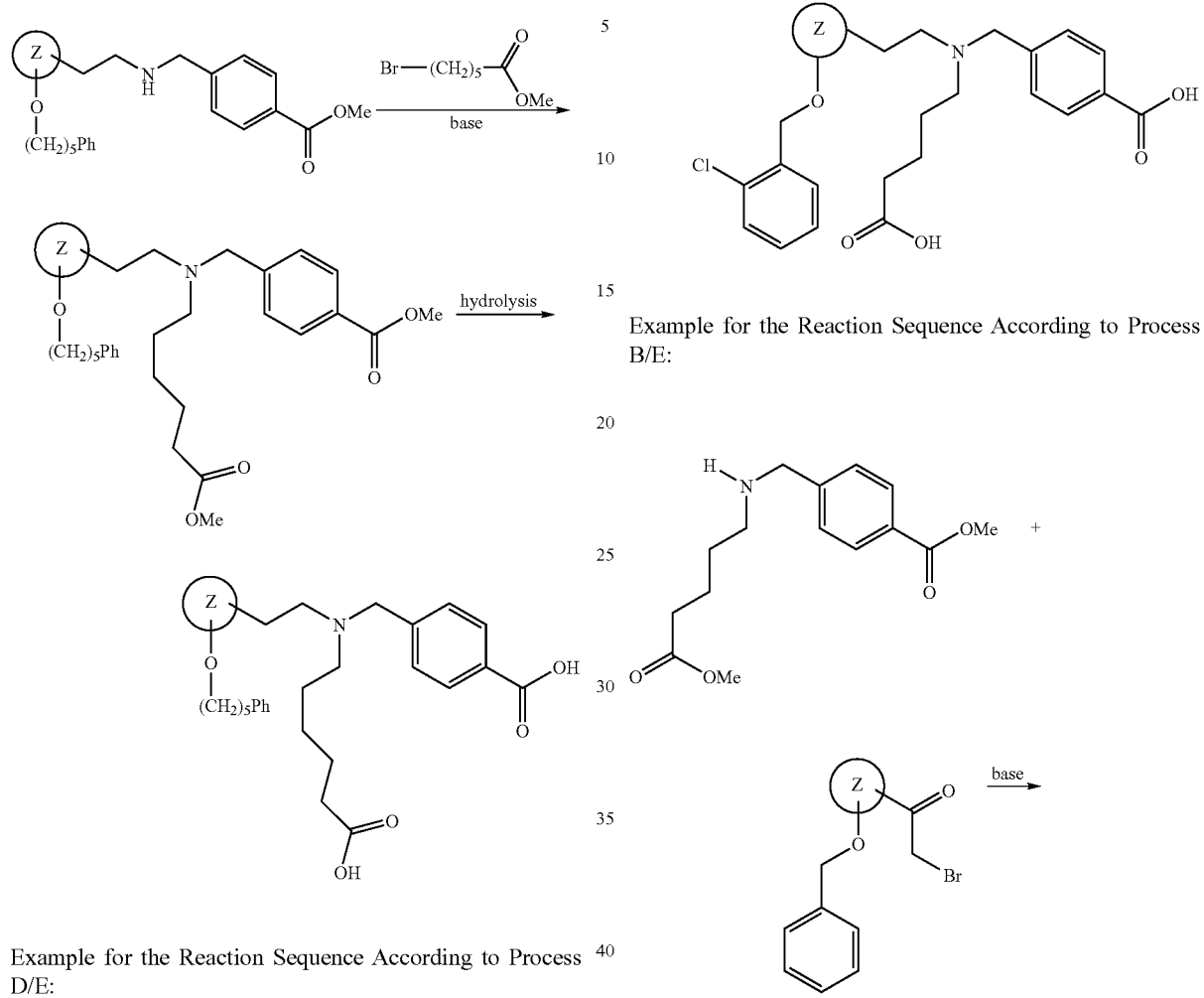
Example for the Reaction Sequence According to Process D/E:
Example for the Reaction Sequence According to Process B/E:
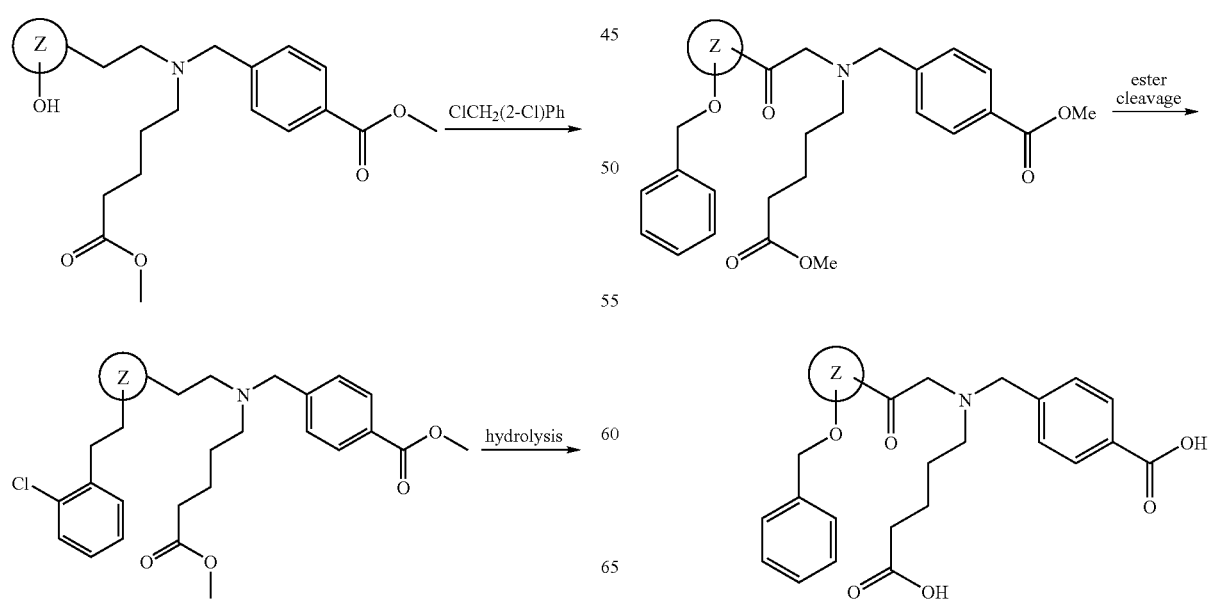

Example for the Reaction Sequence According to Process C/E:
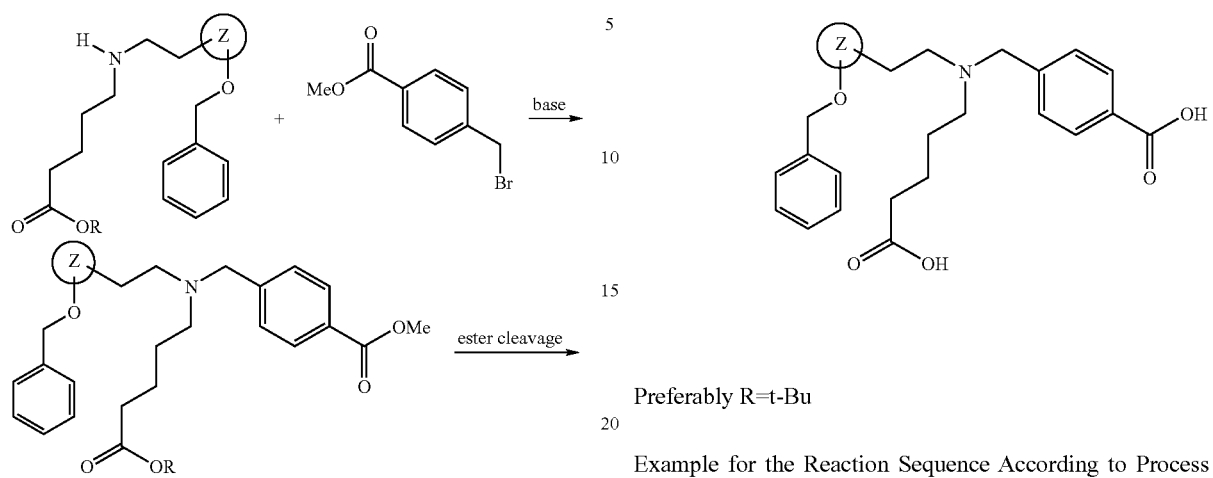
Preferably R=t-Bu
Example for the Reaction Sequence According to Process D/F/E:
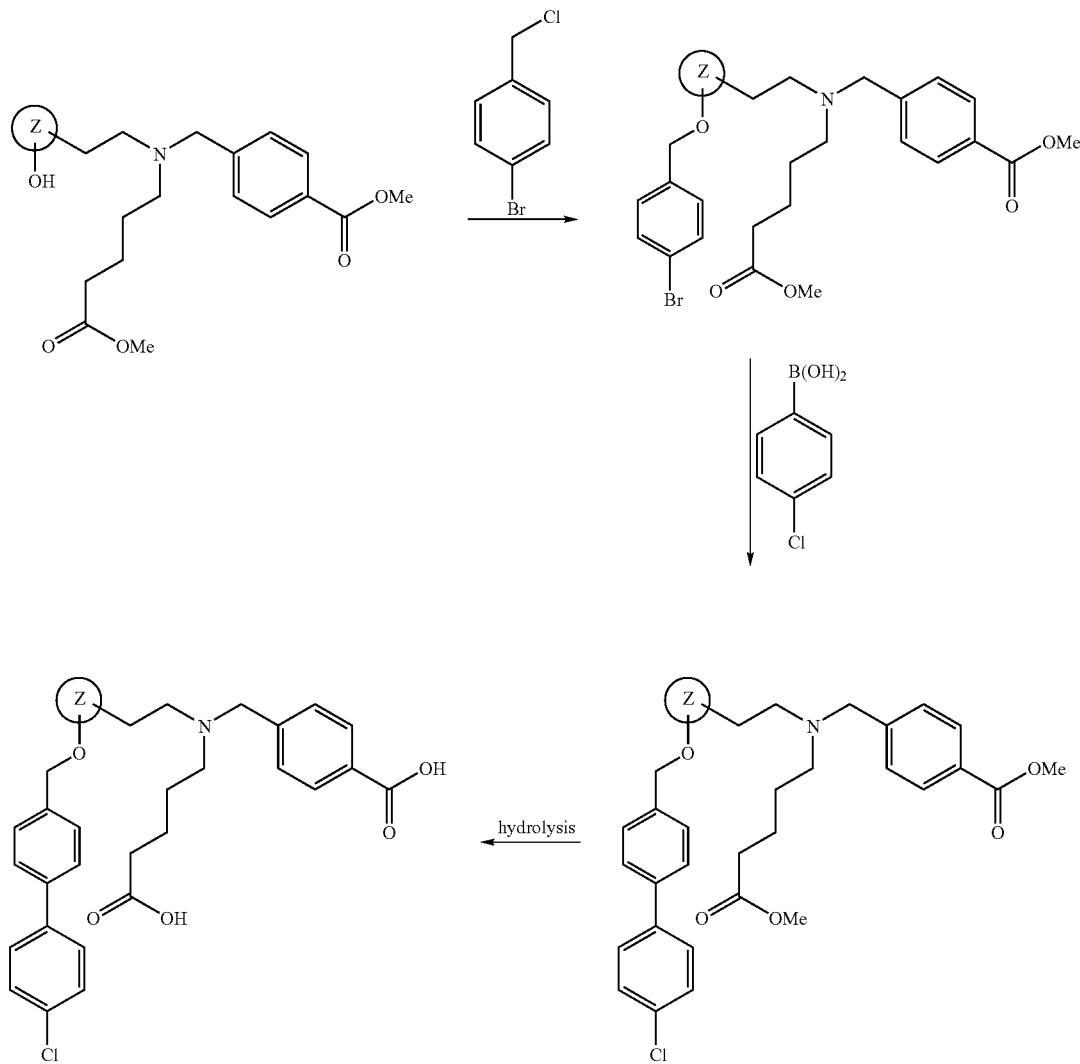

Example for the Reaction Sequence According to Process D/G/E:

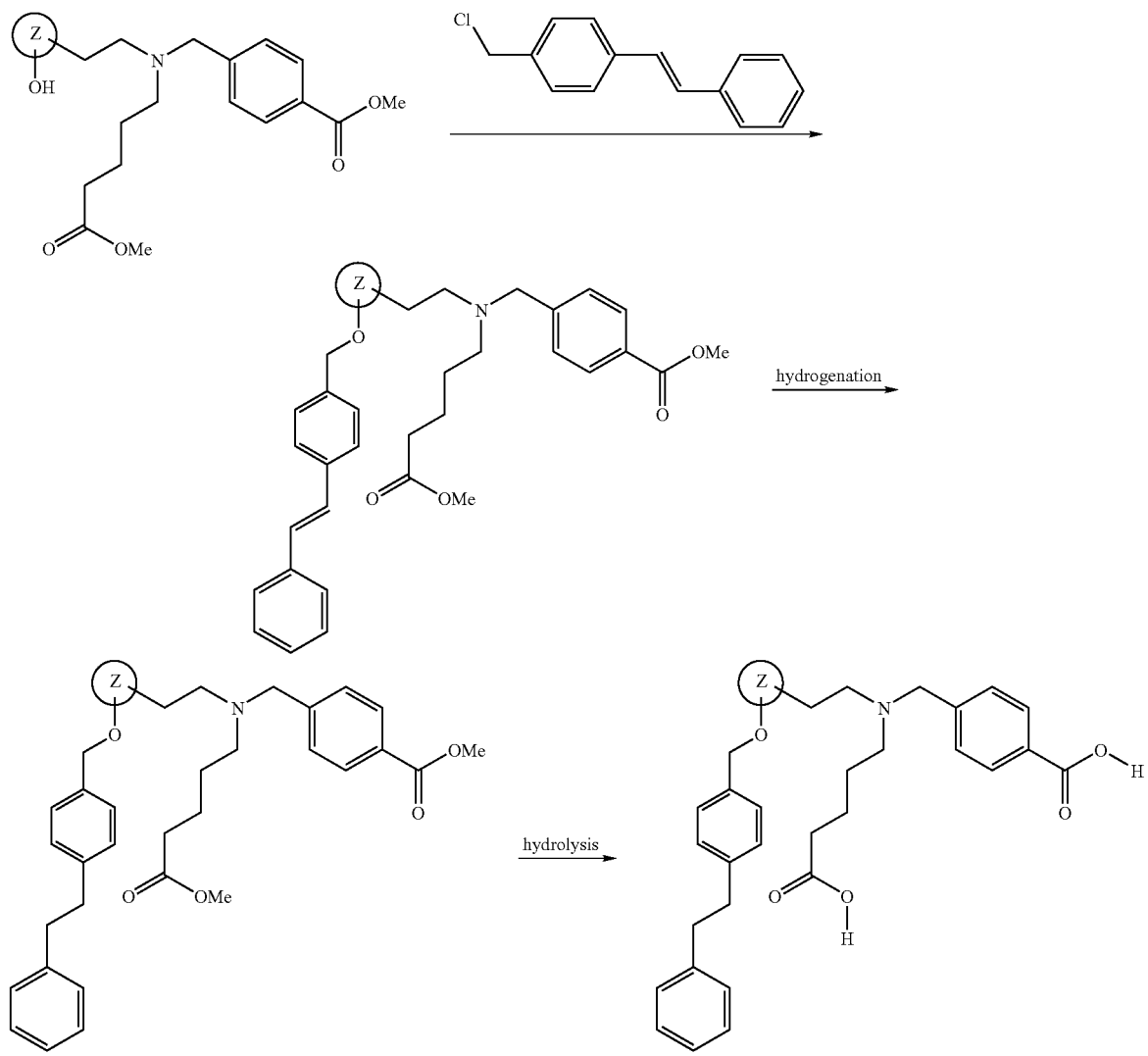

Alternatively, the compounds of the formula (I) can also be prepared on a solid phase, such as a polystyrene resin, particularly preferably a commercially available Wang polystyrene resin. Here, the resin is initially swollen in a solvent such as dimethylformamide (DMF). The appropriate carboxylic acid which serves as starting material is then attached to the resin using standard processes. For example, the carboxylic acid can be attached to the resin in the presence of a base, such as pyridine or 4-dimethylaminopyridine (DMAP), and a reagent which activates the carboxyl unit, such as an acid halide, for example dichlorobenzoyl chloride, in a solvent such as dimethylformamide (DMF). However, it is also possible to use other reagents customarily used for this purpose. The reaction mixture is stirred for at least 2 hours, preferably 12 hours, particularly preferably about 24 hours, at room temperature and atmospheric pressure, an excess of carboxylic acid, preferably a two- to three-fold excess, based on the loading of the solid phase, being used.

After removal of any unreacted reagents, the carboxylic acid attached to the resin can be derivatized without it being necessary to remove the carboxylic acid from the resin beforehand. Thus, for example, an appropriate 4-aminobenzoic acid or 4-formylbenzoic acid derivative can be attached to the resin and then be converted by successive reductive aminations, as described below for the preparation of the compounds of the formula (II), (IV) and (VI), into a compound of the formula (VIII) which can then be converted analogously to process [D] on the solid phase into the target compounds.

Removal from the resin is carried out in a customary manner in acidic medium after the desired synthesis of the target compound on the solid phase. The product which has been cleaved from the resin can, after removal of any solvents present, be purified by known purification processes, such as, for example, chromatographic processes.

The schemes below illustrate possible solid-phase syntheses of compounds of the formula (I); however, other synthesis routes familiar to the person skilled in the art or known from the literature are also possible:

Example A of Solid-phase Synthesis:
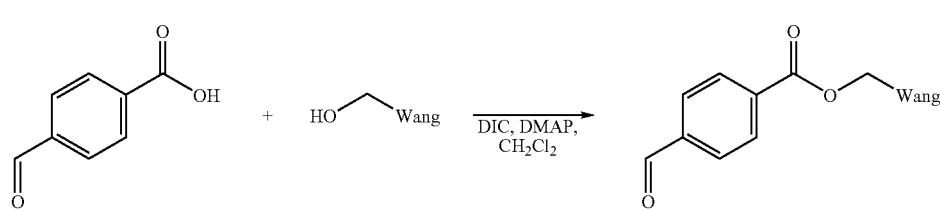
1)
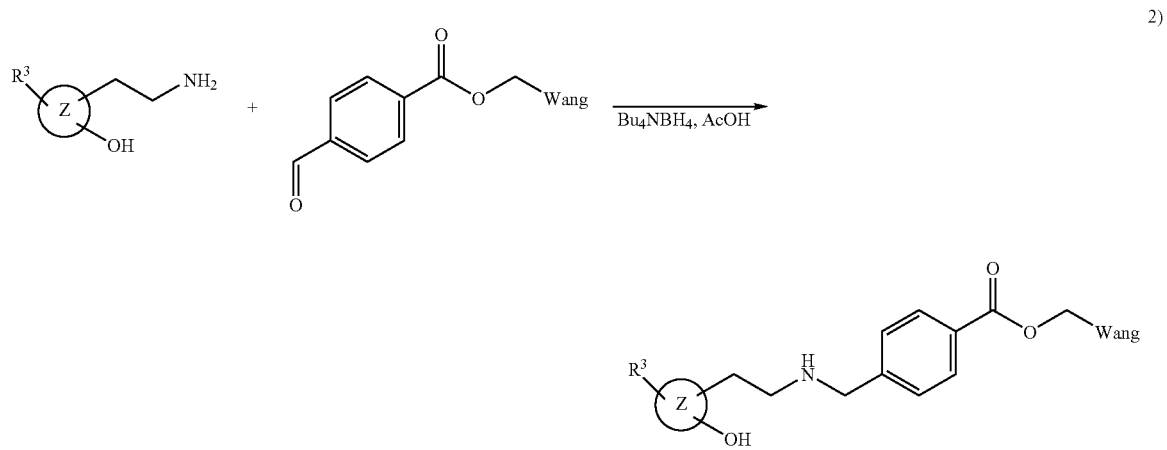
2)
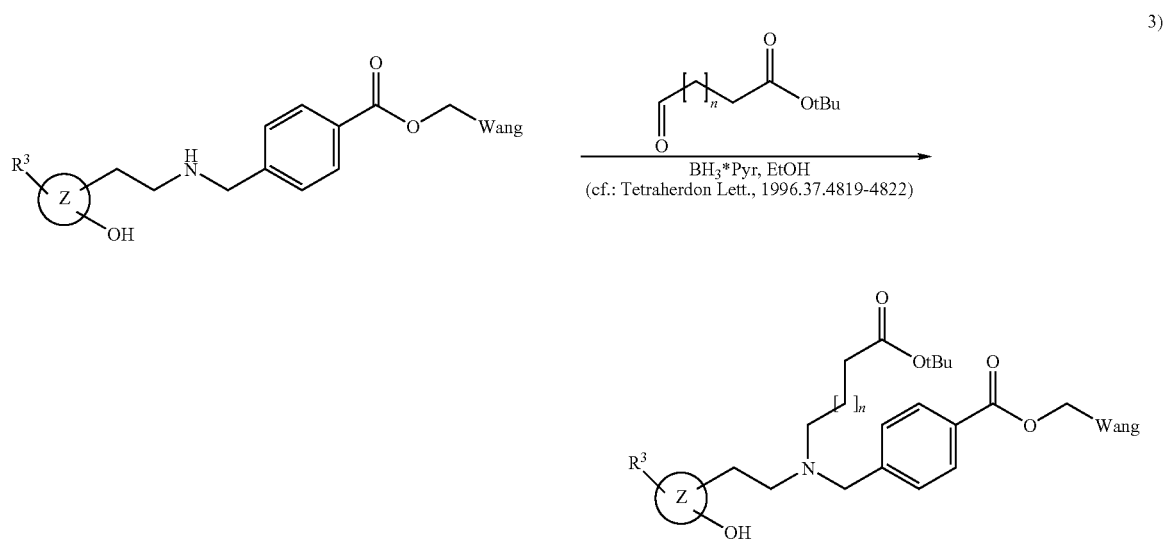
3)
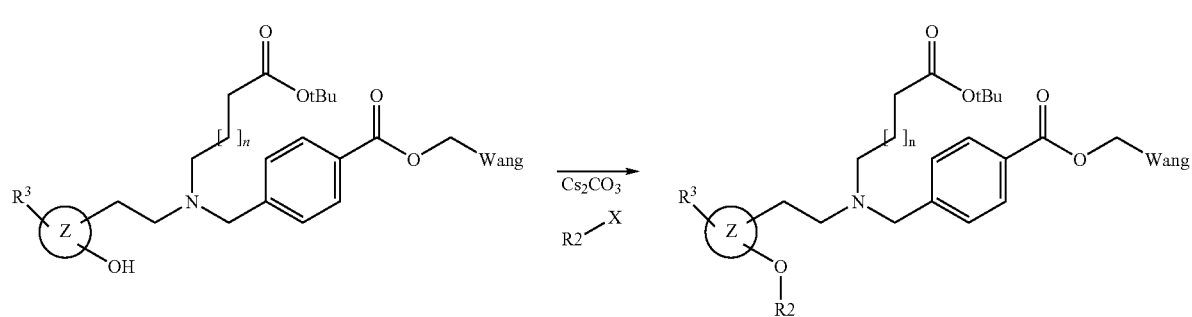
4)

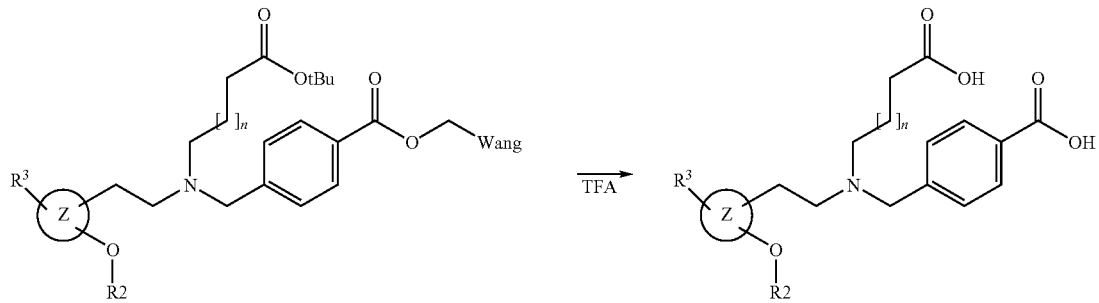
5)
Here, Wang denotes a Wang polystyrene resin.
Example B of Solid-phase Synthesis:
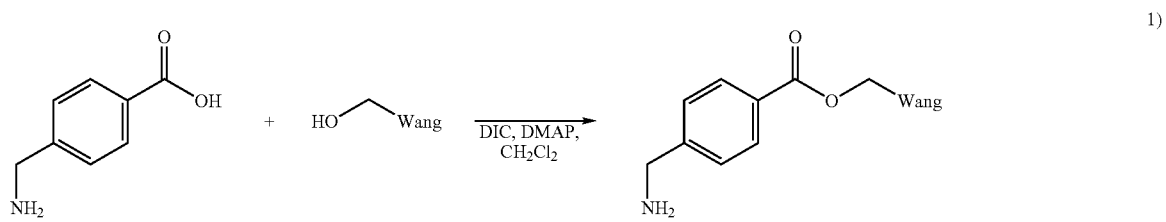
1)
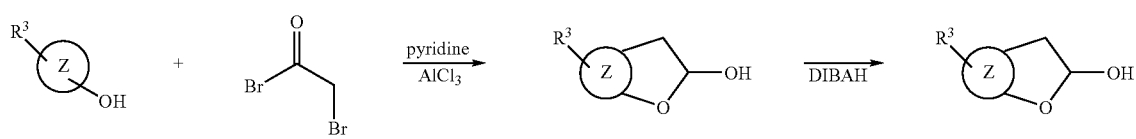
2)
cf. Himbert et al., Chem.Ber.: 121: 1988: 431-432      cf. J. Org. Chem. 1998, 63, 2360-2361.
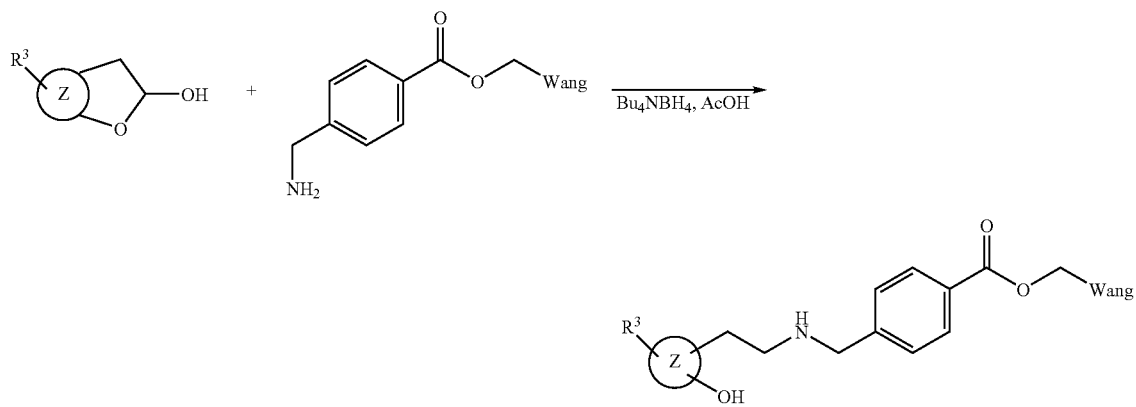
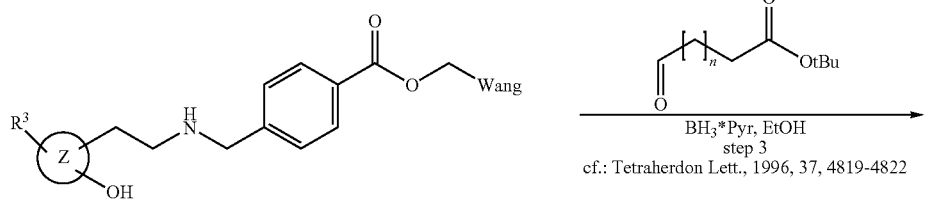
3)

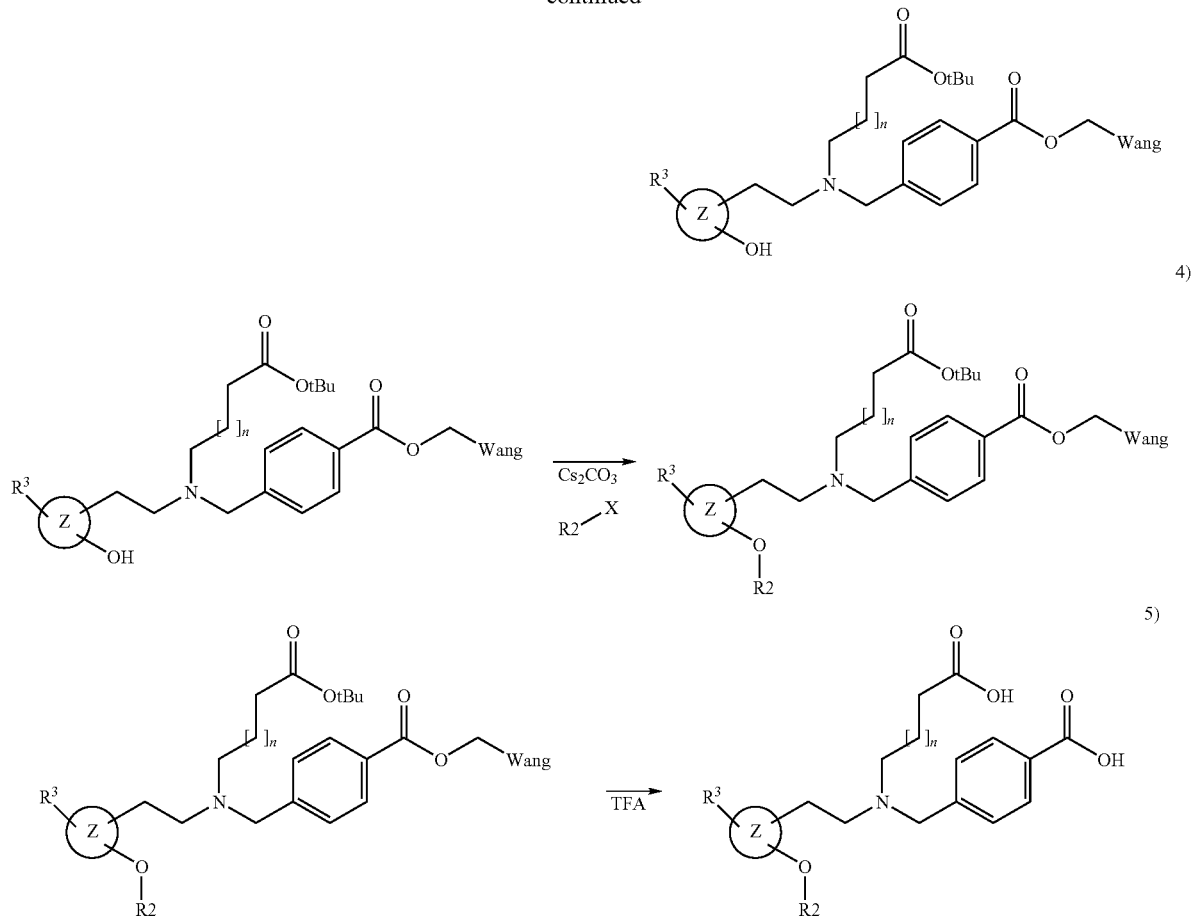

Here, Wang denotes a Wang polystyrene resin.

Preferred solvents for the processes according to the invention are customary organic solvents which do not change under the reaction conditions, or water. For the process according to the invention, preference is given to using ethers, such as diethyl ether, butyl methyl ether, dioxane, tetrahydrofuran, glycol dimethyl ether, or diethylene glycol dimethyl ether, or hydrocarbons, such as benzene, toluene, xylene or petroleum ether, or amides, such as dimethylformamide or hexamethylphosphoric triamide, or 1,3-dimethylimidazolidin-2-one, 1,3-dimethyltetrahydropyrimidin-2-one, acetonitrile, ethyl acetate or dimethyl sulfoxide. It is, of course, also possible to use mixtures of the solvents mentioned above.

Bases which are preferred for the processes according to the invention include basic compounds which are customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t-butoxide, or carbonates, such as sodium carbonate, cesium carbonate or potassium carbonate, or amides, such as sodium amide or lithium diisopropylamide, or organolithium compounds, such as phenyllithium, butyllithium or methyllithium, or sodium hexamethyldisilazane.

The processes A to C according to the invention can preferably be carried out in acetonitrile, in each case by reacting the compounds (II) and (III), (IV) and (V) and (VI) and (VII), respectively, in the presence of a base such as sodium carbonate, $Et_3N$, DABCO, $K_2CO_3$, KOH, NaOH or NaH. The reaction can generally be carried out in a temperature range of from −20° C. to +90° C., preferably of from 0° C. to +70° C. The reaction can be carried out under atmospheric pressure, elevated pressure or reduced pressure (for example in a range of from 0.5 to 5 bar). In general, the reaction is carried out under atmospheric pressure.

In the processes A to C according to the invention, a compound of the formula (I) is prepared by nucleophilic substitution of a leaving group E in one of the compounds of the formula (III), (V) or (VII) by the amine function of one of the compounds of the formula (II), (IV) or (VI). Suitable leaving groups E are, for example: halogen, tosylate, mesylate, or a hydroxyl function which is activated by reagents such as diisopropyl azodicarboxylate/$PPh_3$ (Mitsonobu reaction).

The process D according to the invention can preferably be carried out in acetonitrile by reacting the compounds (VIII) and (IX) in the presence of a base such as sodium carbonate, potassium carbonate, $Et_3N$, DABCO, $K_2CO_3$, KOH, NaOH or NaH. The reaction can generally be carried out in a temperature range of from −20° C. to +90° C., preferably of from 0° C. to +90° C. The reaction can be carried out under atmospheric pressure, elevated pressure or reduced pressure (for example in a range of from 0.5 to 5 bar). In general, the reaction is carried out under atmospheric pressure.

In the process D according to the invention, a compound of the formula (I) is prepared by nucleophilic substitution of a leaving group E in the compound of the formula (IX) by the hydroxyl or thiol function of the compound of the formula (VIII). Suitable leaving groups E are, for example: halogen, tosylate, mesylate, or a hydroxyl function which is activated by reagents such as diisopropyl azodicarboxylate/PPh$_3$ (Mitsonobu reaction).

In the process E according to the invention, a compound of the formula (I) in which $R^1$ and $R^2$ each represent a free carboxyl function is obtained by converting ester and/or nitrile functions of the compound (X) into the corresponding free carboxyl functions. This reaction can be carried out, for example, by adding aqueous solutions of strong acids, such as, for example, HCl or H$_2$SO$_4$, or strong bases, such as, for example, NaOH, KOH or LiOH. The reaction can be carried out in one of the organic solvents mentioned above, in water or in mixtures of organic solvents or in mixtures of organic solvents with water. Preference according to the invention is given, for example, to carrying out the reaction in a mixture of water and methanol or dioxane. In general, the reaction can be carried out in a temperature range of from −20° C. to +90° C., preferably of from 0° C. to +90° C. The reaction can be carried out under atmospheric pressure, elevated pressure or reduced pressure (for example in a range of from 0.5 to 5 bar). In general, the reaction is carried out at atmospheric pressure.

In the process F according to the invention, a compound of the formula (I) is prepared by reacting a compound of the formula (XI) which contains a substitutable group L with a compound of the group (XII) in the presence of a palladium compound and, if appropriate, a reducing agent and further additives in basic medium. Formally, the reaction is a reductive coupling of the compounds of the formulae (XI) and (XII), as described, for example, in L. S. Hegedus, Organometallics in Synthesis, M. Schlosser, Ed., Wiley & Sons, 1994.

Suitable substitutable groups L in the compounds of the formula (XI) are, for example, a halogen radical, such as Br or I, or a customary leaving group, such as, for example, a triflate radical.

The compounds of the formula (XII) contain a reactive group Z which can be selected from the group consisting of —B(OH)$_2$, —C≡CH, —CH═CH$_2$ or —Sn(nBu)$_3$.

Suitable for use as palladium compound are palladium(II) compounds, such as, for example, Cl$_2$Pd(PPh$_3$)$_2$ or Pd(OAc)$_2$ or palladium(0) compounds, such as, for example, Pd(PPh$_3$)$_4$ or Pd$_2$(dba)$_3$. If required, a reducing agent, such as, for example, triphenylphosphine, or other additives, such as, for example, Cu(I)Br, NBu$_4$NCl, LiCl or Ag$_3$PO$_4$, may additionally be added to the reaction mixture (cf. T Jeffery, Tetrahedron lett. 1985, 26, 2667-2670; T. Jeffery, J. Chem. Soc., Chem. Commun. 1984, 1287-1289; S. Bräse, A. deMejiere in "Metal-catalyzed cross-coupling reactions", Ed. F. Diederich, P. J. Stang, Wiley-VCH, Weinheim 1998, 99-166).

The reaction is carried out in the presence of a customary base, such as, for example, Na$_2$CO$_3$, NaOH or triethylamine. Suitable solvents are the organic solvents mentioned above, ethers, such as, for example, dimethoxyethane, being particularly preferred. In general, the reaction can be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out under atmospheric pressure.

In the process G according to the invention, compounds of the formula (I) are obtained by reacting compounds of the formula (XIII), which contain a leaving group E, with compounds of the formula (VIII) according to process D according to the invention, followed by hydrogenation of the resulting compounds of the formula (XIV).

Thus, the first step of process G is analogous to process D, but, instead of the compounds of the formula (IX), compounds of the formula (XIII) are reacted here with the alcohols or thiols of the formula (XIII). This gives the unsaturated compounds of the formula (XIV) which can be converted by customary hydrogenation processes into the compounds of the formula (I).

Preference according to the invention is given to hydrogenation of the compounds of the formula (XIV) with hydrogen in the presence of a catalyst, such as, for example, Pd/carbon or PtO$_2$.

The process G can be carried out in one of the organic solvents mentioned above. Preference is given here to ethyl acetate. In general, the reaction can be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out under atmospheric pressure.

The novel compounds of the formula II, IV and VI can be obtained in a generally known manner by the following methods:

a) by reacting amines of the formulae (XV), (XVI) and (XVII)

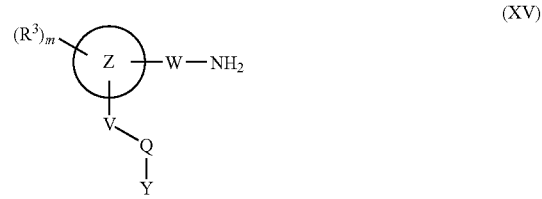

(XV)

(XVI)

(XVII)

where the radicals $R^1$, $R^2$, $R^3$, m, V, Q, U, W, X, Y and A are as defined above;

with carbonyl compounds of the formulae (XVIII), (XIX), (XX)

(XVIII)

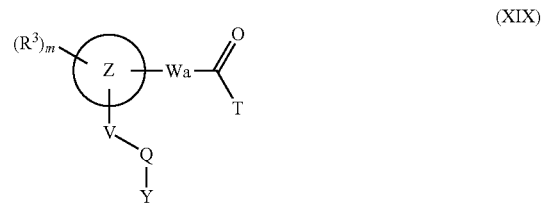

(XIX)

-continued

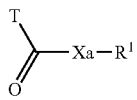
(XX)

where
Ua, Wa and Xa have the meanings of U, W and X, respectively, but are one carbon unit shorter, and
T represents hydrogen or a $C_1$-$C_4$-alkyl function, which may also be attached to Ua or Xa forming a cycle, and the other radicals are as defined above,
are reacted initially giving a Schiff base which is then reduced with customary reducing agents, such as, for example, $NaBH_4$, $H_2/Pd/C$, etc., or reacted directly under the conditions of a reductive alkylation in the presence of a reducing agent, such as, for example, $H_2/Pd/C$, $NaCNBH_3$, $NaH(OAc)_3$ (cf. Patai, Ed., The Chemistry of the Carbon-Nitrogen Double Bond, pp. 276-293 and the literature cited therein);

b) by reacting amines of the formulae (XV), (XVI) and (XVII) with compounds of the formulae (III), (V), (VII) (cf., for example, J. March, Advanced Organic Chemistry, fourth edition, Wiley, 1992, page 411 and the literature cited therein).

Amines of the formula (IIa) or compounds of the formula (VIII)

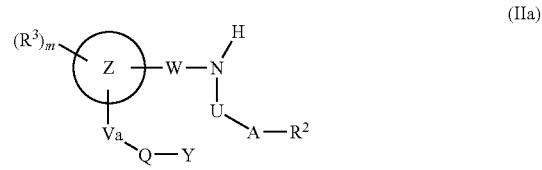
(IIa)

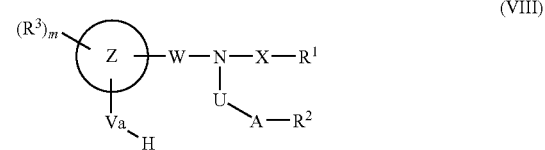
(VIII)

where Va represents O or S,
can be obtained in a generally known manner by the following reaction scheme:

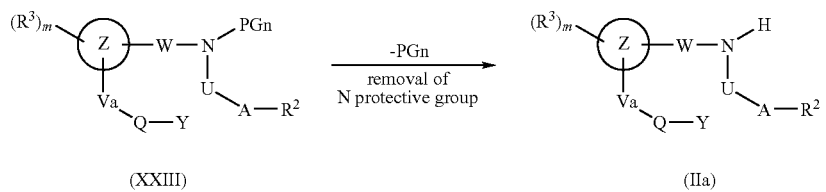

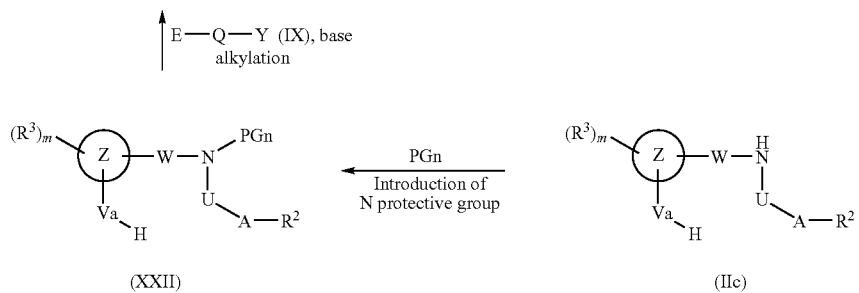

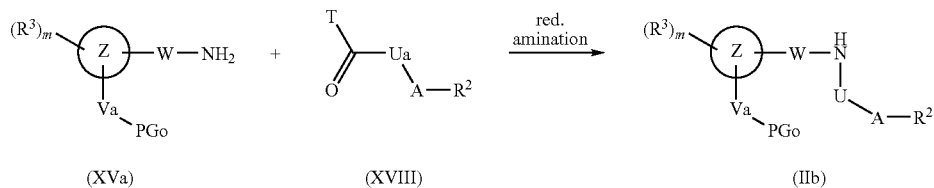

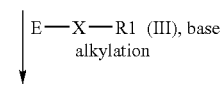

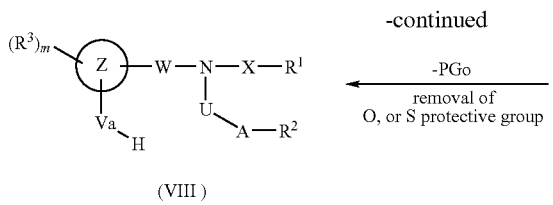

(VIII) ← removal of O, or S protective group -PGo (XXI)

In the scheme above, PGo denotes a customary phenol or thiophenol protective group, such as, for example, $CH_3$, $CH_2Ph$, $CH_2CH=CH_2$, $CH_2OCH_3$, $CH_2OCH_2SiMe_3$, $SiMe_3$, PGn denotes an amine protective group, such as, for example, tBuOCO, T represents hydrogen or a $C_1$-$C_4$-alkyl function, which may also be attached to Ua forming a cycle, and Ua has the meaning of U, but is one $CH_2$ group shorter. The other radicals are as defined above.

(IIb) is obtained, for example, when initially (XVa) is reacted with (XVIII) to give a Schiff base which is then reduced with customary reducing agents, such as, for example, NaBH4, $H_2$/Pd/C, etc., or reacted directly under the conditions of a reductive alkylation in the presence of a reducing agent, such as, for example, $H_2$/Pd/C, $NaCNBH_3$ or NaH (OAc)$_3$. By reaction with a compound of the formula (III) in the presence of a base, the compound (IIb) can be converted into a compound of the formula (XXI) (cf. process A).

An O or S protective group in (IIb) or (XXI) can be removed with a suitable reagent (cf., T. W. Greene, P. G. M. Wuts, Protective Groups in Organic Synthesis, second edition, New York, 1991). If, in formula (IIb) or (XXI), -Va-PGo denotes, for example, —O—$CH_3$, the methyl group can be removed with formation of the phenol using boron tribromide in methylene chloride at from −70° C. to 20° C., using trimethylsilyl iodide in chloroform at 25-50° C. or using sodium ethylthiolate in DMF at 150° C.

From the resulting compound of the formula (IIc), it is possible to obtain a compound of the formula (XXIII) by protecting the amino function (cf. T. W. Greene, P. G. M. Wuts, Protective Groups in Organic Synthesis, second edition, New York, 1991) and subsequently reacting the resulting amino-protected compound of the formula (XXII) with a compound of the formula (IX) (cf. process D).

An N protective group such as in (XXII) can be introduced and removed again by customary methods (cf. T. W. Greene, P. G. M. Wuts, Protective Groups in Organic Synthesis, second edition, New York, 1991). If, in formula (XXII), PGn denotes, for example, tBuOCO, the protective group can be introduced by reacting the amine with tert-butyl pyrrocarbonate in polar or unpolar solvents at from 0° C. to 25° C. The removal of the protective group to give (IIa) can be carried out with a large number of acids, such as, for example, HCl, $H_2SO_4$ or $CF_3COOH$, at from 0° C. to 25° C. (cf. the literature cited above).

Substances of the formulae (III) are commercially available, known from the literature or can be synthesized according to processes known from the literature (cf., for example, J. Chem. Soc. 1958, 3065).

Substances of the formulae (V) are known from the literature or can be synthesized analogously to processes known from the literature (cf., for example, J. Med. Chem. 1989, 32, 1757; Indian J. Chem. Sect. B 1985, 24, 1015; Recl. Trav. Chim. Pays-Bas 1973, 92, 1281; Tetrahedron Lett. 1986, 37, 4327).

Substances of the formula (VII) are commercially available, known from the literature, or can be prepared analogously to processes known from the literature (cf. for example, J. Org. Chem. 1959, 24, 1952; Collect Czech. Chem. Commun 1974, 39, 3527, Helv. Chim. Acta 1975, 58, 682; Liebigs Ann. Chem. 1981, 623).

Substances of the formula (IX) are commercially available, known from the literature, or can be prepared analogously to processes known from the literature (cf., for example, J. prakt. Chem. 1960, 341; Farmaco Ed. Sci. 1956, 378; Eur. J. Med. Chem. Chim. Ther. 1984, 19, 205; Bull, Soc. Chim. Fr. 1951, 97. Liebigs Ann. Chem. 1954, 586, 52; EP-A-0 334 137). In particular, 4-chloromethylbiphenyl compounds which carry a further substituent in the 4'-position can be prepared by coupling 4—(B(OH)$_2$—Ph—CHO with the corresponding 4-substituted bromophenyl compounds in the presence of palladium catalysts, such as, for example, $Pd(PPh_3)_4$ or $PdCl_2$ $(PPh_3)_2$, and sodium carbonate, giving the corresponding biphenyl compounds, and subsequent reduction to the alcohol with $NaBH_4$ and conversion into the corresponding chloride using, for example, $SOCl_2$.

If, in the formulae (III), (V), (VII) and (IX), E represents halogen, the compounds can also be prepared by generally known processes, for example by reacting an alcohol with a chlorinating agent, such as, for example, thionyl chloride or sulfuryl chloride (cf., for example, J. March, Advanced Organic Chemistry, fourth edition, Wiley, 1992, page 1274 and the literature cited therein).

Amines of the formula (XV) are commercially available, known from the literature, or can be synthesized analogously to processes known from the literature (cf., for example, Tetrahedron 1997, 53, 2075; J. Med. Chem. 1984, 27, 1321; WO 97/29079; J. Org. Chem. 1982, 47, 5396). These compounds can be obtained, for example, from the corresponding halide compounds and in particular chloride compounds in which, instead of the radicals W—$NH_2$ of the compounds of the formula (XV), there is a group W'-Hal, where W' is a radical W which is shorter by one C atom, by substitution of the halide radical by a cyano group, giving the corresponding nitrile compounds, and reduction of the nitrile group, or by reacting corresponding aldehyde compounds, in which, instead of the radicals W—$NH_2$ of the compounds of the formula (XV), there is a group W'—CHO, where W' is a radical W which is shorter by one C atom, using nitromethane and subsequent reduction. Some exemplary synthesis routes for the amines of the formula (XV) are shown below, where the given reagents are generally only one of a number of possibilities. Thus, for example, reductions of aldehyde groups to alcohol groups, substitutions of alcohol groups by halogen groups, substitutions of halogen functions by nitrile groups or reductions of nitrile groups to corresponding amino groups can be carried out using all reagents which are customarily employed for such reactions (cf., for example, the appropriate chapters in March, Advanced Organic Chemistry, Wiley, 3th ed., 1985).

In the synthesis routes shown in an exemplary manner below, the given radicals have the same meaning as defined above.

Synthesis Route a):

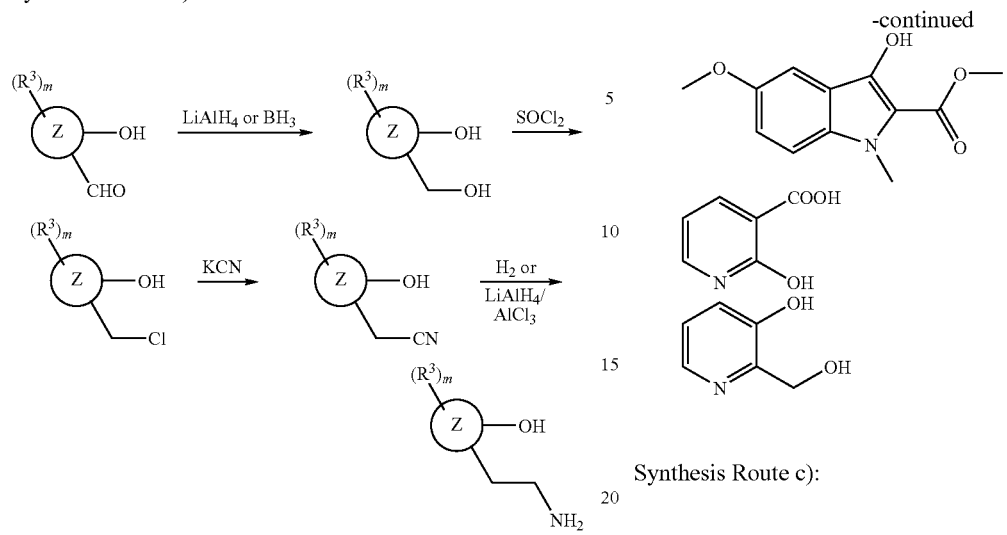

Synthesis Route b):

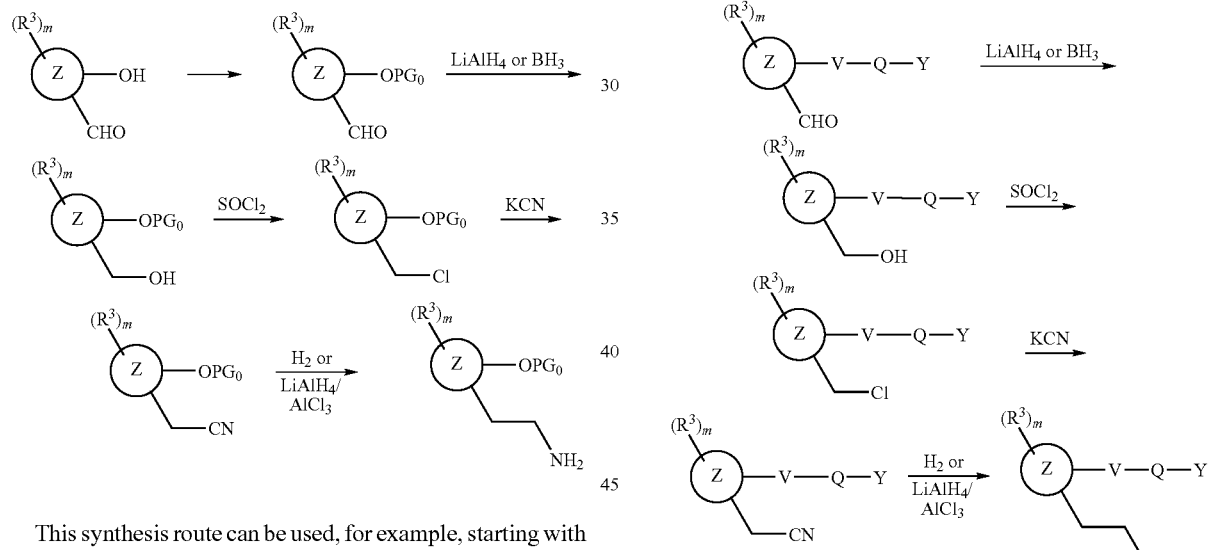

This synthesis route can be used, for example, starting with hydroxycarboxylic acids, which are commercially available or are known from the literature:

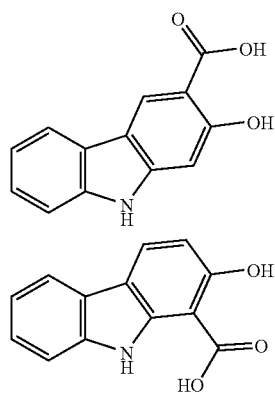

Synthesis Route c):

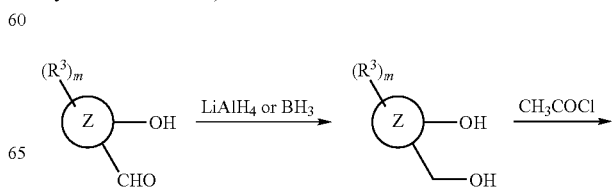

For synthesis routes a) to d), it is also possible to use, instead of the hydroxyaldehydes, the corresponding hydroxycarboxylic acids or hydroxycarboxylic acid esters. In these synthesis routes, it is also possible to convert the primary hydroxyl group into the nitrile group via the corresponding bromide, mesylate, tosylate or acetate instead of via the corresponding halide.

Synthesis Route d):

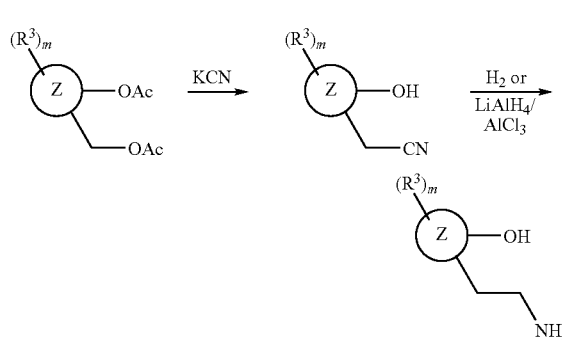

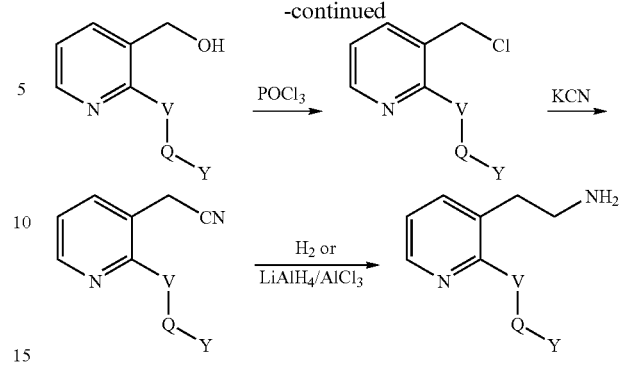

Synthesis Route g):

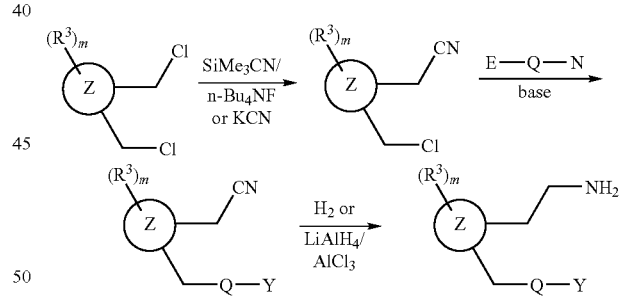

2-Cyanomethyl-3-hydroxypyridine can also be obtained by the method of Desideri et al, J. Heterocycl. Chem. 1988, 333-335.

Synthesis Route h):

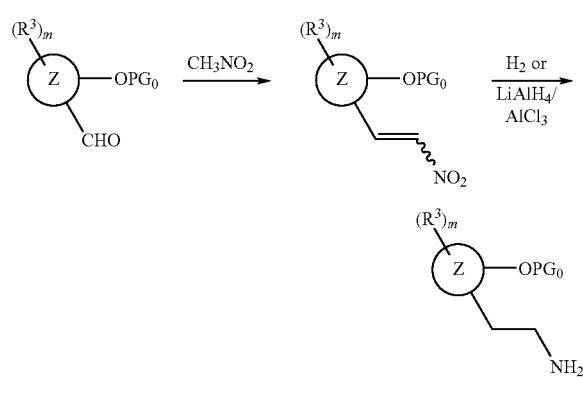

This process can be carried out, for example, starting with 2-hydroxynaphth-1-aldehyde, 1-hydroxymethyl-2-methoxynaphthalene or one of the hydroxyaldehydes below, which are commercially available or known from the literature:

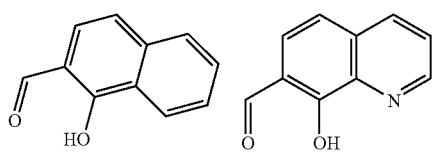

Synthesis Route e):

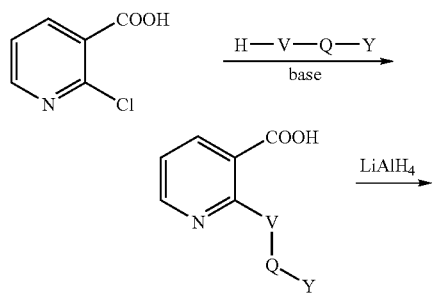

Synthesis Route f):

Amines of the formula (XVI) are commercially available, known from the literature, or can be synthesized analogously to processes known from the literature (cf., for example, J. Am. Chem. Soc. 1982, 104, 6801; Chem. Lett. 1984, 1733; J. Med. Chem. 1998, 41, 5219; DE-2059922).

Amines of the formula (XVII) are commercially available, known from the literature, or can be synthesized analogously to processes known from the literature (cf., for example, J. Org. Chem. 1968, 33, 1581; Bull. Chem. Soc. Jpn. 1973, 46, 968; J. Am. Chem. Soc. 1958, 80, 1510; J. Org. Chem. 1961, 26, 2507; Synth. Commun. 1989, 19, 1787).

Amines of the formulae (XV), (XVI) and (XVII) can also be prepared by generally known processes, for example by reducing a corresponding nitrile, by reacting a corresponding halide with phtalimide and subsequent reaction with hydrazine or by rearranging acyl azides in the presence of water (cf., for example, J. March, Advanced Organic Chemistry, fourth edition, Wiley, 1992, page 1276 and the literature cited therein).

Carbonyl compounds of the formula (XVIII) are commercially available, known from the literature, or can be synthesized analogously to processes known from the literature (cf., for example, J. Med. Chem. 1989, 32, 1277; Chem. Ber. 1938, 71, 335; Bull. Soc. Chim. Fr. 1996, 123, 679).

Carbonyl compounds of the formula (XIX) are commercially available, known from the literature, or can be synthesized analogously to processes known from the literature, (cf., for example, WO 96/11902; DE-2209128; Synthesis 1995, 1135; Bull. Chem. Soc. Jpn. 1985, 58, 2192).

Carbonyl compounds of the formula (XX) are commercially available, known from the literature, or can be synthesized analogously to processes known from the literature (cf., for example, Synthesis 1983, 942; J. Am. Chem. Soc. 1992, 114, 8158).

Carbonyl compounds of the formulae (XVIII), (XIX) and (XX) can also be prepared according to generally known processes, for example by oxidizing alcohols, by reducing acid chlorides or by reducing nitrites (cf., for example, J. March, Advanced Organic Chemistry, fourth edition, Wiley, 1992, page 1270 and the literature cited therein).

Compounds of the formula (XII) are commercially available, known from the literature, or can be synthesized analogously to processes known from the literature (cf., for example, for aromatic boronic acids: J. Chem. Soc. C 1966, 566. J. Org. Chem., 38, 1973, 4016; or for tributyltin compounds: Tetrahedron Lett. 31, 1990, 1347).

Compounds of the formula (XIII) are commercially available, known from the literature, or can be synthesized analogously to processes known from the literature (cf., for example, J. Chem. Soc. Chem. Commun., 17, 1994, 1919).

The compounds according to the invention, in particular the compounds of the general formula (I), show a valuable range of pharmacological effects which could not have been predicted.

The compounds according to the invention, in particular the compounds of the general formula (I), bring about vasorelaxation and an inhibition of platelet aggregation and lead to a reduction in blood pressure and an increase in the coronary blood flow. These effects are mediated by direct stimulation of soluble guanylate cyclase and an intracellular increase in cGMP.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenosis such as after thrombolysis therapies, percutaneous transluminal angioplasties (PTAs), percutaneous transluminal coronary angioplasties (PTCAs), bypass and for the treatment of arteriosclerosis, fibrotic disorders, such as fibrosis of the liver or pulmonary fibrosis, asthmatic disorders and diseases of the urogenital system such as, for example, prostate hypertrophy, erectile dysfunction, female sexual dysfunction and incontinence and also for the treatment of glaucoma.

The compounds described in the present invention, in particular the compounds of the general formula (I), are also active compounds suitable for controlling central nervous system diseases characterized by disturbances of the NO/cGMP system. They are suitable in particular for removing cognitive deficits, for improving learning and memory performances and for treating Alzheimer's disease. They are also suitable for treating disorders of the central nervous system such as states of anxiety, tension and depression, CNS-related sexual dysfunctions and sleep disturbances, and for controlling pathological disturbances of the intake of food, stimulants and addictive substances.

The active compounds are furthermore also suitable for regulating cerebral blood flow and thus represent effective agents for controlling migraine.

They are also suitable for the prophylaxis and control of the sequelae of cerebral infarction (apoplexia cerebri) such as stroke, cerebral ischemias and craniocerebral trauma. The compounds according to the invention, in particular the compounds of the general formula (I), can likewise be employed for controlling states of pain.

In addition, the compounds according to the invention have an anti-inflammatory effect and can therefore be employed as anti-inflammatory agents.

Vasorelaxant Effect in Vitro

Rabbits are anesthetized or killed by intravenous injection of thiopental sodium (about 50 mg/kg) and exsanguinated. The arteria saphena is removed and divided into rings 3 mm wide. The individual rings are in each case mounted on a pair of hooks of triangular shape, open at the ends and made of special wire (Remanium®) having a diameter of 0.3 mm. Under tension, each ring is introduced into a 5 ml organ bath containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10; bovine serum albumin: 0.001%. The force of contraction is detected with Statham UC2 cells, amplified and digitized via A/D converters (DAS-1802 HC, Keithley Instruments, Munich) and recorded in parallel on chart recorders. Contractions are generated by adding phenylephrine.

After several (generally 4) control cycles, the substance to be investigated is added in each further run in increasing dosage in each case, and the height of the contraction reached under the influence of the test substance is compared with the height of the contraction reached in the last preceding run. The concentration necessary to reduce the height of the control value by 50% ($IC_{50}$) is calculated from this. The standard application volume is 5 μl. The DMSO content in the bath solution corresponds to 0.1%.

The results are shown in Table 1:

TABLE 1

| Vasorelaxant effect in vitro | |
|---|---|
| Example | $IC_{50}$ [nM] |
| 3 | 2 |
| 4 | 22 |
| 5 | 7 |
| 9 | 61 |
| 10 | 51 |
| 13 | 94 |
| 16 | 125 |

Stimulation of Recombinant Soluble Guanylate Cyclase (sGC) in Vitro

The investigations of the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out according to the method described in detail in the following literature reference: M. Hoenika, E. M. Becker, H. Apeler, T. Sirichoke, H. Schroeder, R. Gerzer and J-P. Stasch: Purified soluble guanylyl cyclase expressed in a baculovirus/Sf9 system: stimulation by YC-1, nitric oxide, and carbon oxide. J. Mol. Med. 77 (1999): 14-23.

The heme-free guanylate cyclase was obtained by adding Tween 20 to the sample buffer (final concentration 0.5%).

Activation of sGC by a test substance is stated as n-fold stimulation of basal activity.

The present invention includes pharmaceutical preparations which, in addition to non-toxic, inert, pharmaceutically acceptable carriers, comprises the compounds according to the invention, in particular the compounds of the general formula (I), and processes for preparing these preparations.

The active compound, if appropriate in one or more of the carriers listed above, can also be present in microencapsulated form.

The therapeutically effective compounds, in particular the compounds of the general formula (I), should be present in the pharmaceutical preparations detailed above in a concentration of about 0.1 to 99.5, preferably of about 0.5 to 95, % by weight of the complete mixture.

The pharmaceutical preparations detailed above may, apart from the compounds according to the invention, in particular the compounds of the general formula (I), also contain other active pharmaceutical ingredients.

It has generally proved to be advantageous both in human and in veterinary medicine to administer the active compound(s) according to the invention in total amounts of about 0.5 to about 500, preferably 5 to 100, mg/kg of body weight every 24 hours, where appropriate in the form of a plurality of single doses, to achieve the desired results. A single dose contains the active compound(s) according to the invention preferably in amounts of about 1 to about 80, in particular 3 to 30, mg/kg of body weight.

Below, the present invention is illustrated in more detail using non-limiting preferred examples. Unless indicated otherwise, all quantities are stated in percent by weight.

EXAMPLES

Abbreviations

| | |
|---|---|
| RT: | room temperature |
| EA: | ethyl acetate |
| BABA: | n-butyl acetate/n-butanol/glacial acetic acid/phosphate buffer pH 6 (50:9:25.15; org. phase) |

Mobile Phases for Thin-layer Chromatography:

| | |
|---|---|
| T1 E1: | toluene - ethyl acetate (1:1) |
| T1 EtOH1: | toluene - methanol (1:1) |
| C1 E1: | cyclohexane - ethyl acetate (1:1) |
| C1 E2: | cyclohexane - ethyl acetate (1:2) |

Starting Materials

Example I

[4-(Chloromethyl)-2,5-dimethyl-3-thienyl]acetonitrile

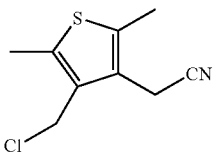

A solution of 2.98 g (14.24 mmol) of 3,4-bis(chloromethyl)-2,5-dimethylthiophene (Gärtner et al., J. Amer. Chem. Soc., 73, 1951, 5872) in 30 ml of dry acetonitrile is, with 1.9 ml (14.24 mmol) of trimethylsilyl cyanide and 12.96 ml (14.42 mmol) of a 1-N-tetra-n-butylammonium fluoride solution in THF, slowly added dropwise and stirred at room temperature overnight. The mixture is then evaporated to dryness using a rotary evaporator and the resulting crude product is purified by column chromatography (cyclohexane/ethyl acetate 10:1). This gives 0.82 g (4.1 mmol, 28% yield) of a colorless oil.

$R_f$ (cyclohexane/ethyl acetate 2:1): 0.39. $^1$H-NMR (200 MHz, CDCl$_3$ δ/ppm): 4.58 (2H, s), 3.64 (2H, s), 2.42 (3H, s), 2.39 (3H, s). MS (DCI, NH$_3$): 234 (M+N$_2$H$_7^+$), 217 (M+NH$_4^+$).

Example II

{4[(4-Bromophenoxy)methyl]-2,5-dimethyl-3-thienyl}acetonitrile

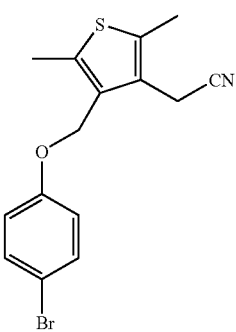

830 mg (6.04 mmol) of anhydrous potassium carbonate are added to a solution of 800 mg (4.33 mmol) of [4-(chloromethyl)-2,5-dimethyl-3-thienyl]acetonitrile from Ex. I and 840 mg (4.83 mmol) of 4-bromophenol in 20 ml of acetonitrile, and the mixture is, under argon, heated at reflux for 12 h. After cooling and removal of the solvent, the resulting crude product is purified by preparative HPLC, giving 1.149 g (3.42 mmol, 85% yield) of a colorless solid.

$R_f$ (cyclohexane/ethyl acetate 2:1): 0.45. $^1$H-NMR (300 MHz, DMSO-d$_6$, δ/ppm): 7.48 (2H, d), 7.01 (2H, d), 4.98 (2H, s), 3.81 (2H, s), 2.38 (3H, s), 2.36 (3H, s). MS (DCI, NH$_3$: 353.1 (M+NH$_4^+$).

Example III

2-{4-[(4-Bromophenoxy)methyl]-2,5-dimethyl-3-thienyl}ethylamine

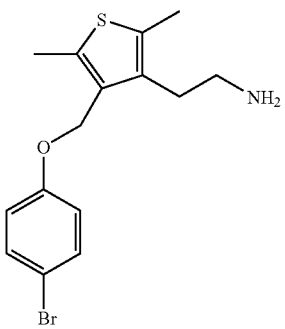

557 mg (4.18 mmol) of aluminum trichloride are dissolved in 10 ml of THF and, under argon, cooled to 0° C., and 2.81 ml of a lithium aluminum hydride solution (1M in THF) are added slowly. A solution of 937 mg (2.79 mmol) of {4[(4-bromophenoxy)methyl]-2,5-dimeethyl-3-thienyl}acetonitrile from Ex. II in 10 ml of THF is then slowly added dropwise to the reaction solution. After 2 h of stirring at room temperature, the reaction solution is cooled to 0° C. and quenched with ice-water, made alkaline using aqueous sodium hydroxide solution, extracted with ethyl acetate and dried over magnesium sulfate. After removal of the solvent, the resulting crude product is purified by preparative HPLC, giving 693 mg (2.04 mmol, 73% yield) of a colorless oil.

$R_f$ (dichloromethane/methanol 10: 1): 0.26. $^1$H-NMR (300 MHz, DMSO-$d_6$, δ/ppm): 7.48 (2H, d), 7.0 (2H, d), 4.86 (2H, s), 3.3 (2H, s broad), 2.65-2.52 (4H, m), 2.32 (3H, s), 2.29 (3H, s). MS (DCI, NH$_3$): 680.9 [2M+H$^+$], 340.1 (M+H$^+$).

Example IV

Methyl 4-{[(2-{4-[(4-bromophenoxy)methyl]-2,5-dimethyl-3-thienyl}ethyl)-amino]methyl}benzoate

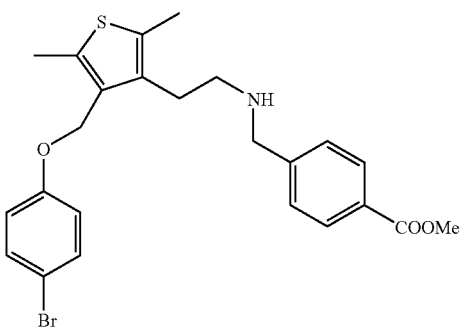

A solution of 640 mg (1.88 mmol) of 2-{4-[(4-bromophenoxy)methyl]-2,5-dimethyl-3-thienyl}ethylamine from Example III and 308 g (1.88 mmol) of methyl 4-formylbenzoate in 5 ml of ethanol is heated at reflux for 2 hours. The solvent is then removed under reduced pressure and the resulting residue is dissolved in 5 ml of methanol. A total of 142 mg (3.76 mmol) of solid NaBH$_4$ are added a little at a time. After two hours of stirring at room temperature, the mixture is poured into water and extracted with ethyl acetate. The organic extract is washed with saturated sodium chloride solution and dried over Na$_2$SO$_4$. After filtration, the solvent is removed under reduced pressure and the resulting crude product is purified by preparative HPLC. This gives 897 mg (1.84 mmol, 97% yield) of a colorless oil.

$R_f$ (cyclohexane/ethyl acetate, 1:1): 0.57. $^1$H-NMR (300 MHz, DMSO-$d_6$, δ/ppm): 8.01 (2H, d), 7.59 (2H, d), 7.42 (2H, d), 6.88 (2H, d), 4.81 (2H, s), 4.23 (2H, pt, including 1H, broad), 3.89 (3H, s), 3.05-2.90 (2H, m), 2.89-2.77 (2H, m), 2.34 (3H, s), 2.31 (3H, s). MS (DCI, NH$_3$): 488.1 (M+H$^+$).

Example V

Methyl 3-[(4-bromobenzyl)oxy]-5,6,7,8-tetrahydro-2-naphthalenecarboxylate

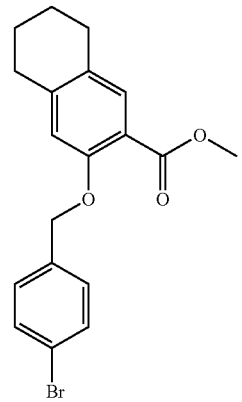

16.1 g (116.4 mmol) of potassium carbonate are added to a solution of 20 g (96.97 mmol) of methyl 3-hydroxy-5,6,7,8-tetrahydro-2-naphthalenecarboxylate (CAS 52888-73-0) and 25.45 g (101.8 mmol) of 4-bromobenzyl bromide in 600 ml of anhydrous acetonitrile, and the mixture is heated at reflux. After 20 hours, most of the solvent is removed using a rotary evaporator and the residue is partitioned between diethyl ether and phosphate buffer (pH 5.5). The organic phase is separated off and dried over anhydrous sodium sulfate. Filtration and concentration using a rotary evaporator give a crude product which is purified by crystallization from ether.

This gives 20.2 g (56% yield) of a colorless solid. $R_f$ (cyclohexane/ethyl acetate 5:1): 0.49. $^1$H-NMR (200 MHz, DMSO-$d_6$, δ/ppm): 12.71 (dd, 4H), 2.63-2.77 (m, 4H), 3.78 (s, 3H), 5.12 (s, 2H), 6.91 (s, 1H), 7.43 (s, 1H), 7.46 (d, 2H), 7.60 (d, 2H). MS (ESI): 375 and 377 (M+H$^+$), 397 and 399 (M+Na$^+$).

Example VI

{3-[(4-Bromobenzyl)oxy]-5,6,7,8-tetrahydro-2-naphthyl}methanol

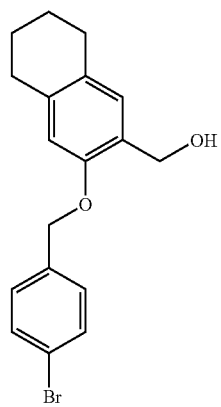

Under argon and at −78° C., a solution of 20.0 g (53.3 mmol) of methyl 3-[(4-bromobenzyl)oxy]-5,6,7,8-tetrahydro-2-naphthalenecarboxylate in 250 ml of anhydrous diethyl ester is admixed with 40 ml (40 mmol) of a one-molar solution of LiAlH4 in ether. Overnight, the mixture is allowed to warm to room temperature. The mixture is then carefully adjusted to pH 1-2 using 2-molar hydrochloric acid and extracted with ether. The organic phase is separated off and dried over anhydrous sodium sulfate. Filtration and concentration using a rotary evaporator gives 16.4 g (89% yield) of a colorless solid.

$R_f$ (cyclohexane/ethyl acetate 5:1): 0.20. $^1$H-NMR (300 MHz, DMSO-d$_6$, δ/ppm): 1.69 (dd, 4H), 2.60-2.68 (m, 4H), 4.47 (d, 2H), 4.90 (t, 1H), 5.03 (s, 2H), 6.67 (s, 1H), 7.03 (s, 1H), 7.40 (d, 2H), 7.59 MS (DCI, NH$_3$): 364 and 366 (M+NH$_4^+$).

Example VII

6-[(4-Bromobenzyl)oxy]-7-(chloromethyl)-1,2,3,4-tetrahydronaphthalene

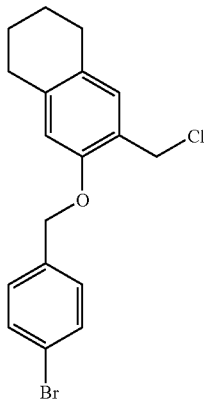

35 ml (473 mmol) of freshly distilled thionyl chloride are added to a solution of 16.4 g (47.23 mmol) of {3-[(4-bromobenzyl)oxy]-5,6,7,8-tetrahydro-2-naphthyl}methanol in 35 ml of dichloromethane. A drop of DMF is added, and the mixture is then heated at reflux for one hour. The solvent and excess thionyl chloride are then distilled off. The residue is recrystallized from ether which contains a little cyclohexane. This gives 17.2 g (99% yield) of a yellow solid.

$R_f$ (cyclohexane/ethyl acetate 1:1): 0.78. $^1$H-NMR (300 MHz, DMSO-d$_6$, δ/ppm): 1.69 (dd, 4H), 2.60-2.70 (m, 4H), 4.67 (s, 2H), 5.10 (s, 2H), 6.77 (s, 1H), 7.07 (s, 1H), 7.43 (d, 2H), 7.60 (d, 2H). MS (DCI, NH$_3$): 382 (M+NH$_4^+$).

Example VIII

{3-[(4-Bromobenzyl)oxy]-5,6,7,8-tetrahydro-2-naphthyl}acetonitrile

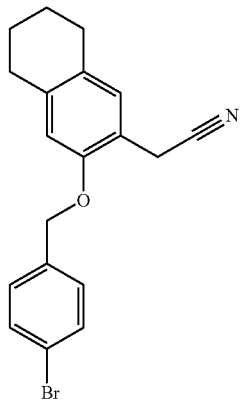

2.78 g (56.77 mmol) of sodium cyanide are added to a solution of 17.3 g (47.31 mmol) of 6-[(4-bromobenzyl)oxy]-7-(chloromethyl)-1,2,3,4-tetrahydronaphthalene in 850 ml of dimethylformamide, and the mixture is stirred at room temperature overnight. Water is then added, and the mixture is extracted with ether. The organic phase is dried over anhydrous sodium sulfate. Filtration and concentration using a rotary evaporator give 13.89 g (82% yield) of product.

$R_f$ (cyclohexane/ethyl acetate 3:1): 0.51. $^1$H-NMR (300 MHz, DMSO-d$_6$, δ/ppm): 1.69 (dd, 4H), 2.61-2.70 (m, 4H), 3.80 (s, 2H), 5.10 (s, 2H), 6.80 (s, 1H), 7.01 (s, 1H), 7.46 (d, 2H), 7.59 (d, 2H). MS (DCI, NH$_3$): 373 and 375 (M+NH$_4^+$).

Example IX

2-{3-[(4-Bromobenzyl)oxy]-5,6,7,8-tetrahydro-2-naphthyl}ethylamine

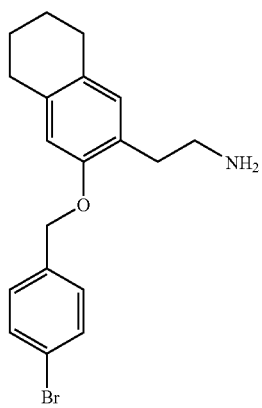

38 ml of a 2-molar solution of borane/dimethyl sulfide complex in tetrahydrofuran (THF) are added to a solution of 13.5 g (37.89 mmol) of {3-[(4-bromobenzyl)oxy]-5,6,7,8-tetrahydro-2-naphthyl}acetonitrile in 300 ml of anhydrous THF. The mixture is heated at reflux for 5 hours. After cooling, the mixture is acidified with dilute hydrochloric acid and once more heated briefly (5 minutes). The mixture is then made alkaline using aqueous sodium hydroxide solution and extracted with ether. The organic extract is dried over anhydrous sodium sulfate. Filtration and concentration using a rotary evaporator give 14.2 g of a yellow wax-like solid which is only about 92% pure but, in spite of this, is used without purification for the next step.

$R_f$ (cyclohexane/ethyl acetate 3:1) 0.81. $^1$H-NMR (300 MHz, DMSO-$d_6$, δ/ppm): 1.68 (dd, 4H), 2.03 (s broad, 2H), 2.57-2.70 (m, 8H), 5.01 (s, 2H), 6.67 (s, 1H), 6.80 (s, 1H), 7.40 (d, 2H), 7.59 (d, 2H). MS (DCI, NH$_3$): 360 and 362 (M+H$^+$).

Example X

Methyl 4-{[(2-{3-[(4-bromobenzyl)oxy]-5,6,7,8-tetrahydro-2-naphthyl}ethyl)amino]methyl}benzoate

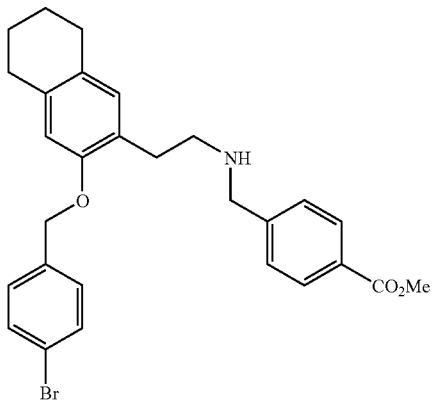

A solution of 14.84 g (41.18 mmol) of 2-{3-[(4-bromobenzyl)oxy]-5,6,7,8-tetrahydro-2-naphthyl}ethylamine and 6.08 g (37.06 mmol) of methyl 4-formylbenzoate in 300 ml of toluene is heated at reflux in a water separator for 30 minutes. The toluene is then removed using a rotary evaporator and the residue is taken up in methanol. 2.34 g (61.77 mmol) of solid sodium borohydride are added with ice-cooling to the methanolic solution. The mixture is stirred at room temperature for 30 minutes and then neutralized with 5% strength sodium dihydrogen phosphate solution, diluted with water and extracted with ether. The organic phase is dried over sodium sulfate. The crude product obtained after filtration and concentration using a rotary evaporator is purified by silica gel flash chromatography using the mobile phase cyclohexane/ethyl acetate 2:1. This gives 5.62 g (27% yield).

$R_f$ (cyclohexane/ethyl acetate 1: 1): 0.26. $^1$H-NMR (300 MHz, DMSO-$d_6$, δ/ppm): 1.68 (dd, 4H), 2.56-2.68 (m, 8H), 3.74 (s, 2H), 3.83 (s, 3H), 4.99 (s, 2H), 6.66 (s, 1H), 6.79 (s, 1H), 7.33 (d, 2H), 7.41 (d, 2H), 7.53 (d, 2H), 7.87 (d, 2H). MS (ESI): 508 and 510 (M+H$^+$).

Example XI

Methyl 4-{[(2-{3-[(4-bromobenzyl)oxy]-5,6,7,8-tetrahydro-2-naphthyl}ethyl)(5-methoxy-5-oxopentyl)amino]methyl}benzoate

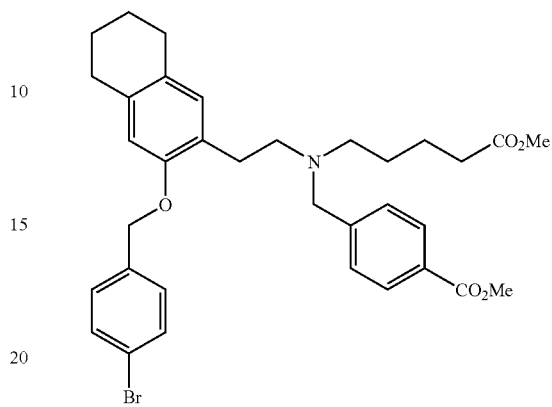

2.3 g (4.52 mmol) of methyl 4-{[(2-{3-[(4-bromobenzyl)oxy]-5,6,7,8-tetrahydro-2-naphthyl}ethyl)amino]methyl}benzoate, 1.06 g (5.43 mmol) of methyl bromovalerate and 0.75 g (5.43 mmol) of potassium carbonate in 150 ml of butyronitrile are heated at reflux. After 48 hours, the reaction has ended. The mixture is evaporated to dryness. The residue is then taken up in ethyl acetate and washed with water. The organic phase is dried over sodium sulfate. After filtration and concentration using a rotary evaporator, the crude product is purified by silica gel flash chromatography using the mobile phase cyclohexane/ethyl acetate 6:1. This gives 622 mg (60% yield) of a colorless oil.

$R_f$ (cyclohexane/ethyl acetate 1:1): 0.53 $^1$H-NMR (300 MHz, DMSO-$d_6$, δ/ppm): 1.32-1.47 (m, 4H), 1.67 (dd, 4H), 2.17 (t, 2H), 2.39 (t, 2H), 2.50-2.69 (m, 8H), 3.54 (s, 3H), 3.58 (s, 2H), 3.82 (s, 3H), 4.92 (s, 2H), 6.63 (s, 1H), 6.75 (s, 1H), 7.31 (d, 2H), 7.36 (d, 2H), 7.52 (d, 2H), 7.82 (d, 2H). MS (ESI): 622 and 624 (M+H$^+$).

Example XII

{$^3$-[(4-Bromobenzyl)oxy]-6-methyl-2-pyridinyl}methanol

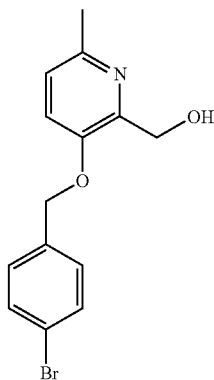

9.58 g (69.31 mmol) of anhydrous potassium carbonate are added to a solution of 3.86 g (37.73 mmol) of 2-(hydroxymethyl)-6-methyl-3-pyridinol and 8.32 g (33.27 mmol) of 4-bromobenzyl bromide in 50 ml of acetonitrile, and the mixture is, under argon, heated at reflux for 12 h. After cooling and removal of the solvent, the resulting crude product is purified by column chromatography (cyclohexane/ethyl acetate 2/1), giving 7.205 g (23.38 mmol, 82% yield) of a colorless solid.

$^1$H-NMR (300 MHz, DMSO-d$_6$, δ/ppm): 7.59 (2H, d), 7.42 (2H, d), 7.35 (1H, d), 7.1 (1H, d), 5.14 (2H, s), 4.79 (1H, t), 4.55 (2H, d), 2.4 (3H, s). MS (DCI, NH$_3$): 308/310 (M+H$^+$).

Example XIII

3-[(4-Bromobenzyl)oxy]-2-(bromomethyl)-6-methylpyridine

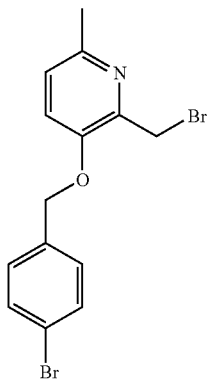

A solution of 7.205 g (23.38 mmol) of {3-[(4-bromobenzyl)oxy]-6-methyl-2-pyridinyl}methanol in 160 ml of THF is added to a solution of 9.2 g (35.07 mmol) of triphenylphosphine and 11.63 g (35.07 mmol) of carbon tetrabromide in 320 ml of THF. After 5 hours of stirring at room temperature, a further 3.066 g of triphenylphosphine and 3.877 g of carbon tetrabromide (in each case 0.5 equivalents) are added in solid form. After 12 hours, the mixture is evaporated to dryness, taken up in ether and filtered through kieselguhr, the organic phase is concentrated by evaporation and the resulting product is isolated by flash chromatography (silica gel, dichloromethane). This gives 2.028 g (5.46 mmol, 23% yield) of a colorless solid.

R$_f$ (cyclohexane/ethyl acetate 1:1): 0.35. $^1$H-NMR (400 MHz, DMSO-d$_6$, δ/ppm): 7.61 (2H, d), 7.46 (2H, d), 7.43 (1H, d), 7.19 (1H, d), 5.21 (2H, s), 4.64 (2H, s), 2.38 (3H, s). MS (DCI, NH$_3$): 370/372 (M+H$^+$).

Example XIV

{3-[(4-Bromobenzyl)oxy]-6-methyl-2-pyridinyl}acetonitrile

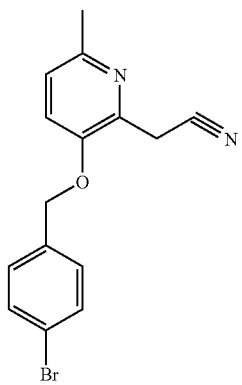

2.99 ml (22.45 mmol) of trimethylsilyl cyanide and 22.45 ml (22.45 mmol) of a 1-N-tetra-n-butylammonium fluoride solution in THF are slowly added dropwise to a solution of 5.55 g (14.97 mmol) of 3-[(4-bromobenzyl)oxy]-2-(bromomethyl)-6-methylpyridine in 350 ml of dry acetonitrile, and the mixture is stirred at room temperature overnight. The mixture is then evaporated to dryness using a rotary evaporator and the resulting crude product is purified by column chromatography (cyclohexane/ethyl acetate 1.5:1). This gives 4.29 g (13.53 mmol, 90% yield) of a colorless oil.

R$_f$ (cyclohexane/ethyl acetate 2:1): 0.21. $^1$H-NMR (200 MHz, CDCl$_3$, δ/ppm): 7.59 (2H, d), 7.45 (2H, d), 7.42 (1H, d), 7.29 (1H, d), 5.19 (2H, s), 4.09 (2H, s), 2.4 (3H, s). MS (DCI, NH$_3$): 632.7/634.8 (2M+H$^+$), 317 (M+H$^+$).

Example XV

2-{3-[(4-Bromobenzyl)oxy]-6-methyl-2-pyridinyl}ethylamine

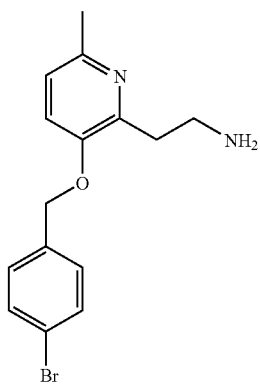

At 0° C., 525 μl (30.76 mmol) of a borane-dimethyl sulfide complex solution are slowly added dropwise to a solution of 3.25 g (10.25 mmol) of {3-[(4-bromobenzyl)-oxy]-6-methyl-2-pyridinyl}acetonitrile in 50 ml of THF. After thawing and two hours of stirring at room temperature, the reaction solution is cooled to 0° C. and quenched with a 1-N-HCl solution. The mixture is then evaporated to dryness using a rotary evaporator, taken up in ethyl acetate and made alkaline using aqueous sodium hydroxide solution. The organic phase is dried over magnesium sulfate, and, after removal of the solvent, the resulting crude product is purified by column chromatography (dichloromethane/methanol/acetic acid 100:10:1.5), giving 325 mg (1.01 mmol, 10% yield) of a colorless oil.

$R_f$ (dichloromethane/methanol 10:1): 0.05. LC-MS: Rt=1.524 min, MS (ESI): 321 (M+H$^+$). LC-MS method: Column: Symmetry C 18; 21 mm×150 mm; 5 μm Ionization: ESI positive/negative Oven temperature: 70° C. Solvent A: acetonitrile Solvent B: 0.3 g of HCl (30%)/1 l of water Gradient: A/B 2/98 to 95/5 over a period of 2.5 min Flow rate: 0.9 ml/min to 1.2 ml/min over a period of 2 min MS (DCI, NH$_3$): 321.1/323.1 (M+H$^+$).

Example XVI

Methyl 4-{[(2-{3-[(4-bromobenzyl)oxy]-6-methyl-2-pyridinyl}ethyl)amino]methyl}benzoate

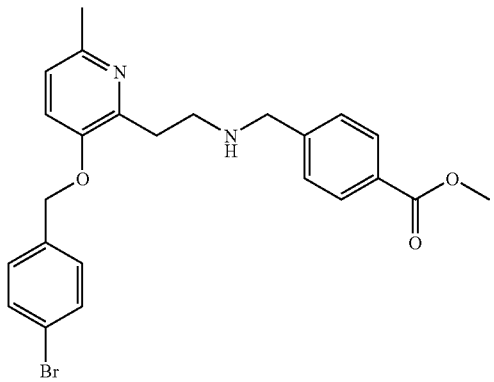

A solution of 675 mg (2.10 mmol) of 2-{3-[(4-bromobenzyl)oxy]-6-methyl-2-pyridinyl}ethylamine and 345 mg (2.10 mmol) of methyl 4-formylbenzoate in 5 ml of ethanol is heated at reflux for two hours. The solvent is then removed under reduced pressure and the resulting residue is dissolved in 5 ml of methanol. A total of 159 mg (4.21 mmol) of solid NaBH$_4$ are added a little at a time. After two hours of stirring at room temperature, the mixture is poured into water and extracted with ethyl acetate. The organic extract is washed with saturated sodium chloride solution and dried over Na$_2$SO$_4$. After filtration, the solvent is removed under reduced pressure and the resulting crude product is purified by preparative HPLC. This gives 351 mg (0.75 mmol, 35% yield) of a colorless oil.

$^1$H-NMR (200 MHz, DMSO-d$_6$, δ/ppm): 7.90 (2H, d), 7.56 (2H, d), 7.46 (2H, d), 7.37 (2H, d), 7.29 (1H, d), 7.02 (1H, d), 5.08 (2H, s), 3.80 (3H, s), 3.41-3.12 (2H, s broad), 2.99-2.71 (4H m), 2.36 (3H, s). MS (ESI): 469 (M+H$^+$).

Example XVII

Methyl 4-{[(2-{3-[(4-bromobenzyl)oxy]-6-methyl-2-pyridinyl}ethyl)(5-ethoxy-5-oxopentyl)amino]methyl}benzoate

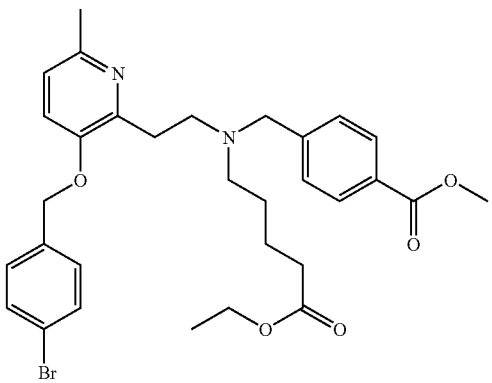

134 mg (1.27 mmol) of anhydrous sodium carbonate are added to a solution of 298 mg (0.63 mmol) of methyl 4-{[(2-{3-[(4-bromobenzyl)oxy]-6-methyl-2-pyridinyl}ethyl)amino]methyl}benzoate and 150 μl (0.95 mmol) of methyl 5-bromovalerate in 3 ml of acetonitrile, and the mixture is heated at reflux for 12 hours. The mixture is then concentrated by evaporation, taken up in ethyl acetate and washed with water. After drying over Na$_2$SO$_4$, filtration and concentration, the product is purified by preparative HPLC. This gives 293 mg (0.49 mmol, 77% yield) of a colorless oil.

$^1$H-NMR (300 MHz, DMSO-d$_6$, δ/ppm): 7.83 (2H, d), 7.54 (2H, d), 7.39-7.22 (5H, m), 7.0 (1H, d), 5.02 (2H, s), 3.99 (2H, q), 3.61 (2H, s), 3.29 (3H, s), 2.92-2.81 (2H, m), 2.76-2.64 (2H, m), 2.39 (2H, t), 2.32 (3H, s), 2.12 (2H, t), 1.42-1.26 (4H, m), 1.18 (3H, t). LC-MS: Rt=3.45 min; MS (ESIpos): 597/599 (M$^+$). LC-MS method: HPLC unit: HP 1100 UV detector DAD: 208-400 nm Column: Symmetry C18; 50 mm×2.1 mm; 3.5 μm Ionization: ESI positive/negative Oven temperature: 40° C. Solvent A: CH$_3$CN+0.1% formic acid Solvent B: H$_2$O+0.1% formic acid Gradient:

| Time | A % | B % | Flow rate |
|---|---|---|---|
| 0.00 | 10.0 | 90.0 | 0.50 |
| 4.00 | 90.0 | 10.0 | 0.50 |
| 6.00 | 90.0 | 10.0 | 0.50 |
| 6.10 | 10.0 | 90.0 | 1.00 |
| 7.50 | 10.0 | 90.0 | 0.50 |

SYNTHESIS EXAMPLES

Example 1

Methyl 4-{[(2-{4-[(4-bromophenoxy)methyl]-2,5-dimethyl-3-thienyl}ethyl)(5-ethoxy-5-oxopentyl)amino]methyl}benzoate

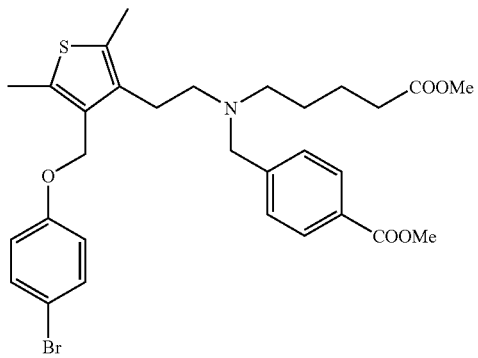

365 mg (3.45 mmol) of anhydrous sodium carbonate are added to a solution of 842 mg (1.72 mmol) of methyl 4-{[2-{4-[(4-bromophenoxy)methyl]-2,5-dimethyl-3-thienyl}ethyl)amino]methyl}benzoate from Ex. IV and 409 μl (2.59 mmol) of methyl 5-bromovalerate in 10 ml of acetonitrile, and the mixture is heated at reflux for 12 hours. The mixture is then concentrated by evaporation, taken up in ethyl acetate and washed with water. After drying over $Na_2SO_4$, filtration and concentration, the product is purified by preparative HPLC. This gives 1.058 g (1.71 mmol, 93% yield) of a colorless oil.

$R_f$ (cyclohexane/ethyl acetate 2:1): 0.44. $^1$H-NMR (200 MHz, DMSO-$d_6$, δ/ppm): 7.99 (2H, d), 7.67 (2H, d), 7.43 (2H, d), 6.91 (2H, d), 4.83 (2H, s), 4.46 (2H, s), 4.03 (2H, q), 3.89 (3H, s), 3.18-2.78 (6H, m), 2.34 (3H, s), 2.27 (3H, s), 2.16 (2H, t), 1.72-1.51 (2H, m), 1.49-1.29 (2H, m), 1.19 (3H, t). MS (ESI): 616 (M+H$^+$).

Example 2

Methyl 4-{[[2-(4-{(2',4'-dichloro-1,1'-biphenyl-4-yl)oxy]methyl}-2,5-dimethyl-3-thienyl)ethyl](5-ethoxy-5-oxopentyl)amino]methyl}benzoate

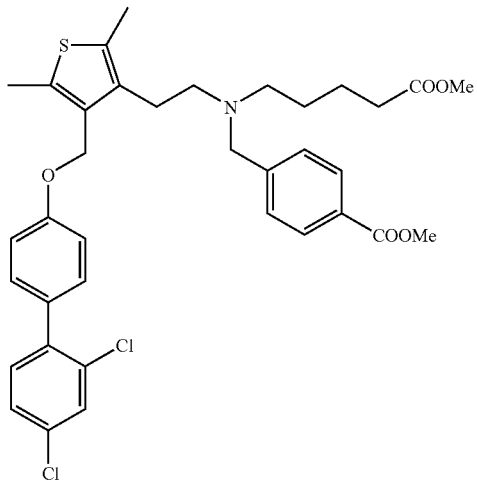

120 mg (0.19 mmol) of methyl 4-{[(2-{4-[(4-bromophenoxy)methyl]-2,5-dimethyl-3-thienyl}ethyl)(5-ethoxy-5-oxopentyl)amino]methyl}benzoate from Ex. 1 are dissolved in 2 ml of 1,2-dimethoxyethane, and 44 mg (0.23 mmol) of 2,4-dichlorophenylboronic acid, 7 mg (0.01 mmol) of bis(triphenylphoshine)-palladium(II) chloride and 215 μl of a 2-molar solution of $Na_2CO_3$ in water are added under argon. The reaction mixture is then stirred under reflux for 12 h. The mixture is then cooled and filtered through 1 g of Extrelute, the filter cake is washed with dichloromethane and the filtrate is concentrated using a rotary evaporator. The resulting product is purified by preparative HPLC. This gives 73 mg (0.11 mmol, 53% yield) of a colorless oil.

$R_f$ (cyclohexane/ethyl acetate 2:1): 0.51. $^1$H-NMR (300 MHz, DMSO-$d_6$, δ/ppm): 8.01 (2H, d), 7.71 (1H, d), 7.64 (2H, d), 7.49 (1H, dd), 7.41 (1H, s), 7.36 (2H, d), 7.00 (2H, d), 4.89 (2H, s), 4.47 (2H, s), 4.00 (2H, q), 3.84 (3H, s), 3.21-2.71 (6H, m), 2.37 (3H, s), 2.28 (3H, s), 2.14 (2H, t), 169-1.51 (2H, m), 1.48-1.31 (2H, m), 1.13 (3H, t). MS (ESI): 681.9 (M+H$^+$).

Example 3

4-({(4-Carboxybutyl)[2-(4-{[(2',4'-dichloro-1,1'-biphenyl-4-yl)oxy]methyl}-2,5-dimethyl-3-thienyl)ethyl]amino}methyl)benzoic acid

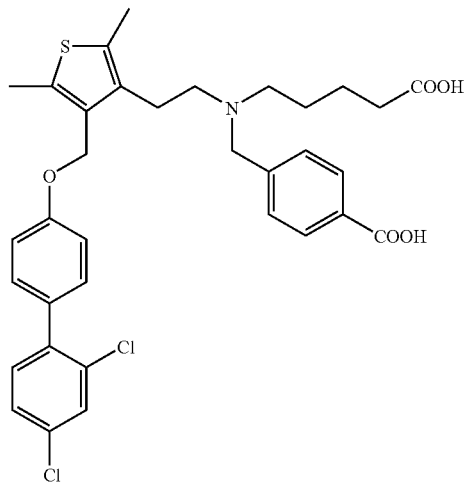

500 μl of a 45% strength solution of NaOH in water are added to a solution of 68 mg (0.1 mmol) of methyl 4-{[[2-(4-{(2',4'-dichloro-1,1'-biphenyl-4-yl)oxy]methyl}-2,5-dimethyl-3-thienyl)ethyl](5-ethoxy-5-oxopentyl)amino]methyl}benzoate from Ex. 2 in 4.0 ml of dioxane and 2 ml of water, and the mixture is stirred at 90° C. for 2 hours. After cooling, the dioxane is removed under reduced pressure and the aqueous phase is adjusted to pH 4 to 5 using 1-molar hydrochloric acid. This results in the precipitation of the product, which is filtered off, washed with water and dried. This gives 47 mg (0.07 mmol, 72% yield) of a white solid.

$R_f$(ethyl acetate/methanol, 7:3): 0.22. $^1$H-NMR (200 MHz, DMSO-$d_6$, δ/ppm): 12.4 (2H, broad), 7.84 (2H, d), 7.70 (1H, d), 7.53-7.29 (6H, m), 7.03 (2H, d), 4.82 (2H, s), 3.61 (2H, s), 2.71-2.38 (6H, m, partially obscured by DMSO), 2.35 (3H, s), 2.18 (3H, s), 2.08 (2H, t)), 1.48-1.28 (4H, m). MS (ESI): 639.9 (M+H$^+$).

The following compounds were prepared in an analogous manner:

| Ex. | Formula | Analytical data |
|---|---|---|
| 4 (from 1 and 4-trifluoro-methylphenyl-boronic acid and then analogously to Ex. 2 and 3) | 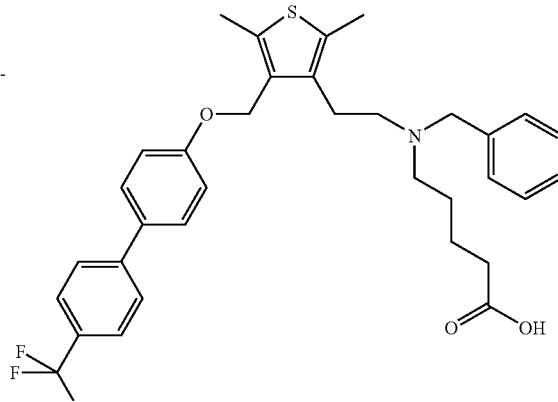 | $^1$H-NMR: δ [ppm] (DMSO-$d_6$): 12.31 (1H, broad), 9.99 (1H, broad), 8.08-7.91 (2H, m), 7.89-7.72 (6H, m), 7.67 (2H, d), 7.08 (2H, d), 4.89 (2H, s), 3.45 (2H, s), 3.22-2.88 (4H, m), 2.60-2.00 (10H, m, including 2.39 (3H, s), 2.27 (3H, s), 2.08 (2H, t)), 1.76-1.49 (2H, m), 1.48-1.29 (2H, m). (200 MHz) |
| 5 (from 1 and 4-methoxy-phenylboronic acid and then analogously to Ex. 2 and 3) | 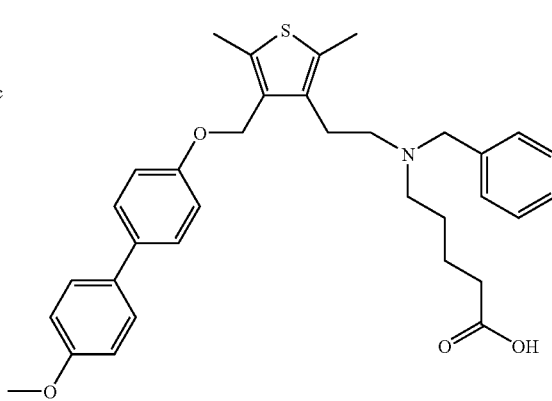 | $^1$H-NMR: δ [ppm] (DMSO-$d_6$): 12.4 (2H, broad), 7.53 (6H, dd), 6.98 (6H, d), 4.81 (2H, s), 3.79 (3H, s), 3.60 (2H, s), 2.71-2.02 (16H, m, partially obscured by DMSO, including 2.37 (3H, s), 2.21 (3H, s), 2.09 (2H, t)), 1.48-1.28 (4H, m). (200 MHz) |
| 6 (from 1 and 4-chlorophenyl-boronic acid and then analogously to Ex. 2 and 3) | 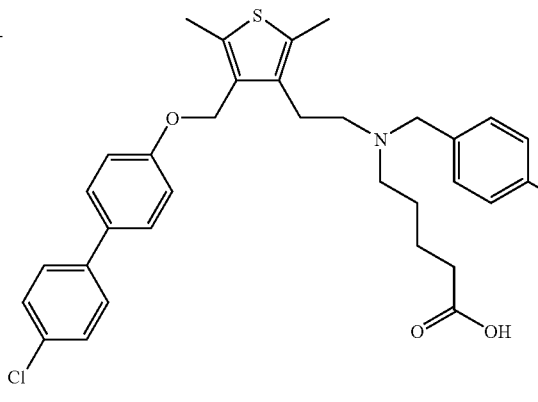 | $^1$H-NMR: δ [ppm] (DMSO-$d_6$): 12.2 (2H, broad), 7.82 (2H, d), 7.61 (4H, t), 7.49 (2H, d), 7.35 (2H, d), 7.03 (2H, d), 4.71 (2H, s), 3.60 (2H, s), 2.71-2.37 (6H, m, partially obscured by DMSO), 2.35 (3H, s), 2.19 (3H, s), 2.08 (2H, t)), 1.46-1.31 (4H, m). (200 MHz) |
| 7 (from 1 and 4-fluoro-phenylboronic acid and then analogously to Ex. 2 and 3) | 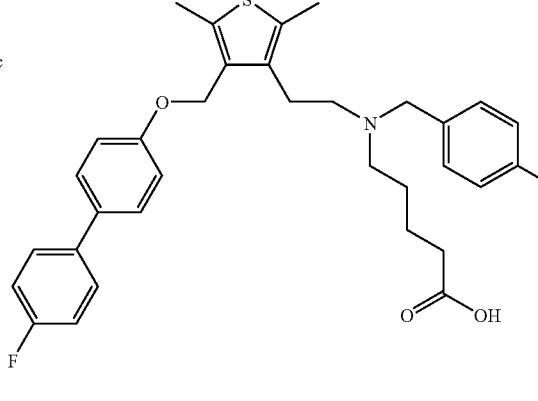 | $^1$H-NMR: δ [ppm] (DMSO-$d_6$): 12.5 (1H, broad), 10.05 (1H, broad), 8.08-7.77 (2H, m), 7.71-7.51 (6H, m), 7.38 (2H, t), 7.02 (2H, d), 4.86 (2H, s), 4.48 (2H, s), 3.20-2.69 (4H, m), 2.60-2.02 (10H, m, partially obscured by DMSO, including 2.36 (3H, s), 2.27 (3H, s), 2.09 (2H, t)), 1.48-1.29 (4H, m). (200 MHz) |

| Ex. | Formula | Analytical data |
|---|---|---|
| 8 (from 1 and 4-carboxy-phenylboronic acid and then analogously to Ex. 2 and 3) | 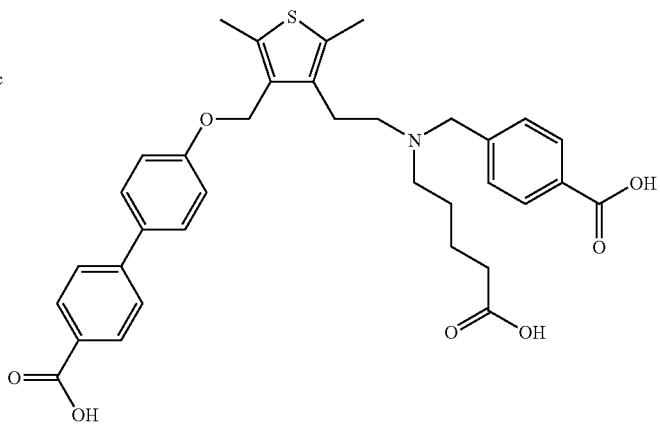 | MS: 616.1 (M + H⁺) |
| 9 (from 1 and 4-t-butylphenyl-boronic acid and then analogously to Ex. 2 and 3) | 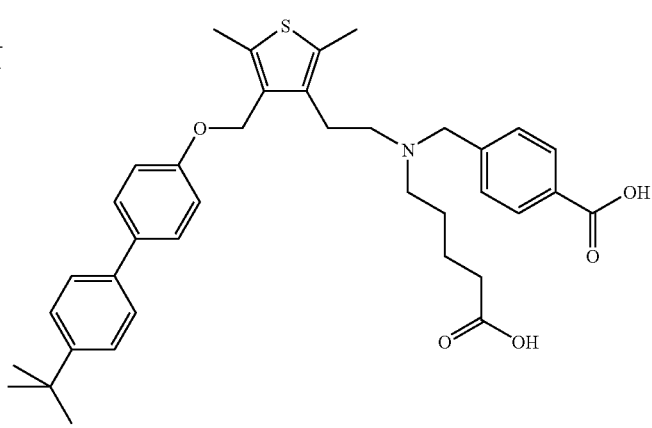 | MS: 628.1 (M + H⁺) |
| 10 (from 1 and 3-methoxy-phenylboronic acid and then analogously to Ex. 2 and 3) | 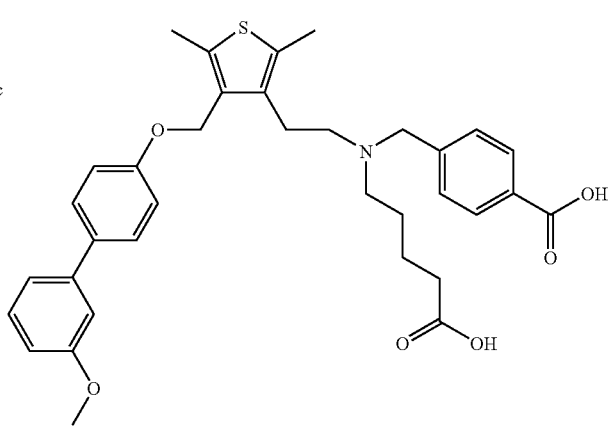 | $^1$H-NMR: δ [ppm] (DMSO-$d_6$): 12.2 (1H, broad), 10.05 (1H, broad), 8.09-7.78 (2H, m), 7.59 (2H, d), 7.41-7.29 (2H, m), 7.22-7.09 (2H, m), 7.01 (2H, d), 6.91 (2H, d), 4.87 (2H, s), 4.46 (2H, s), 3.82 (3H, s), 3.21-2.89 (4H, m), 2.59-2.02 (10H, m, partially obscured by DMSO, including 2.38 (3H, s), 2.28 (3H, s), 2.09 (2H, t)), 1.48-1.28 (4H, m). (200 MHz) |

Example 11

Methyl 4-{[(2-{3-[(4'-methoxy-1,1'-biphenyl-4-yl)methoxy]-5,6,7,8-tetrahydro-2-naphthyl}-ethyl)(5-methoxy-5-oxopentyl)amino]methyl}benzoate

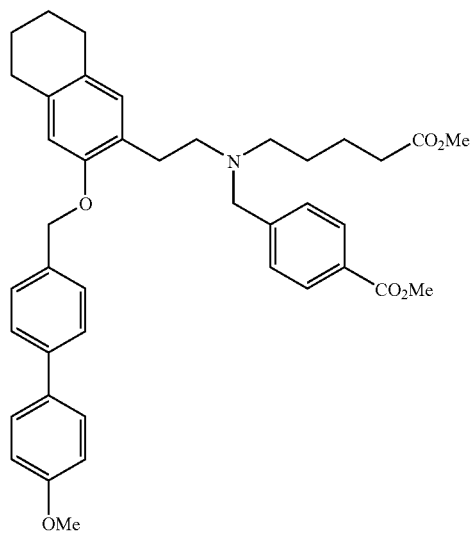

56.5 mg (0.35 mmol) of 4-methoxyphenylboronic acid and 0.48 ml of a 2-molar solution of sodium carbonate in water are added to a solution of 200 mg (0.32 mmol) of methyl 4-{[(2-{3-[(4-bromobenzyl)oxy]-5,6,7,8-tetrahydro-2-naphthyl}ethyl)(5methoxy-5-oxopentyl)amino]methyl}benzoate and 11.1 mg (3 mol %) of tetrakis(triphenylphosphine)palladium-(0) in 10 ml of dimethoxyethane (DME). Under argon, the mixture is heated at reflux for three hours. pH5 phosphate buffer and ether are then added. The phases are separated. The aqueous phase is extracted with ether. The combined ether phases are dried over sodium sulfate, filtered and concentrated using a rotary evaporator. The product is isolated by silica gel flash chromatography using the mobile phase cyclohexane/ethyl acetate 8:1. This gives 160 mg (77% yield) of a pale yellow oil.

$R_f$ (cyclohexane/ethyl acetate 5:1): 0.10. $^1$H-NMR (400 MHz, DMSO-$d_6$, δ/ppm): 1.58-1.72 (m, 8H), 2.16 (t, 2H), 2.41 (t, 2H), 2.55-2.59 (m, 4H), 2.63-2.69 (m, 4H), 3.52 (s, 3H), 3.60 (s, 2H), 3.81 (s, 6H), 5.00 (s, 2H), 6.69 (s, 1H), 6.77 (s, 1H), 7.02 (d, 2H), 7.37 (d, 2H), 7.41 (d, 2H), 7.58 (2d, 4H), 7.83 (d, 2H). MS (ESI): 650 (M+H$^+$).

Example 12

Methyl 4-({(5-methoxy-5-oxopentyl)[2-(3-{[4'-(trifluoromethyl)-1,1'-biphenyl-4-yl]-methoxy}-5,6,7,8-tetrahydro-2-naphthyl)ethyl]amino}methyl)benzoate

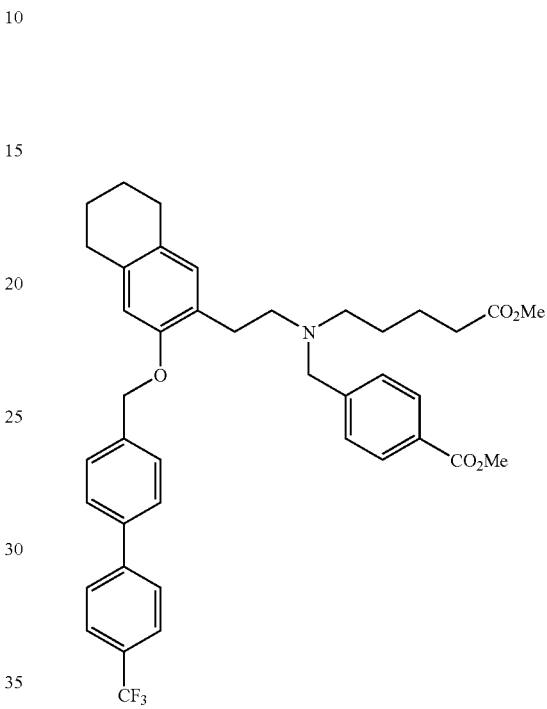

In a manner analogous to that described for Synthesis Example 11, 200 mg (0.32 mmol) of methyl 4-{[(2-{3-[(4-bromobenzyl)oxy]-5,6,7,8-tetrahydro-2-naphthyl}ethyl)(5-methoxy-5-oxopentyl)amino]methyl}benzoate, 11.1 mg (3 mol %) of tetrakis(triphenylphosphine)palladium-(0), 70.6 mg (0.35 mmol) of 4-(trifluoromethyl)phenylboronic acid and and 0.48 ml of a 2-molar solution of sodium carbonate in 10 ml of DME give, after silica gel flash chromatography (cyclohexane/ethyl acetate 10:1), 170 mg (67% yield) of a light-yellow oil.

$R_f$ (cyclohexane/ethyl acetate 5:1): 0.16. $^1$H-NMR (200 MHz, DMSO-$d_6$, δ/ppm): 1.61-1.72 (m, 8H), 2.13 (t, 2H), 2.40 (t, 2H), 2.50-2.70 (m, 4H, partially obscured by DMSO signal), 3.50 (s, 3H), 3.60 (s, 2H), 3.79 (s, 3H), 5.03 (s, 2H), 6.69 (s, 1H), 6.78 (s, 1H), 7.36 (d, 2H), 7.49 (d, 2H), 7.71 (d, 2H), 7.79-7.86 (m, 6H). MS (ESI): 688 (M+H$^+$).

Example 13

4-{[(4-Carboxybutyl)(2-{3-[(4'-methoxy-1,1'-biphenyl-4-yl)methoxy]-5,6,7,8-tetrahydro-2-naphthyl}ethyl)amino]methyl}benzoic acid

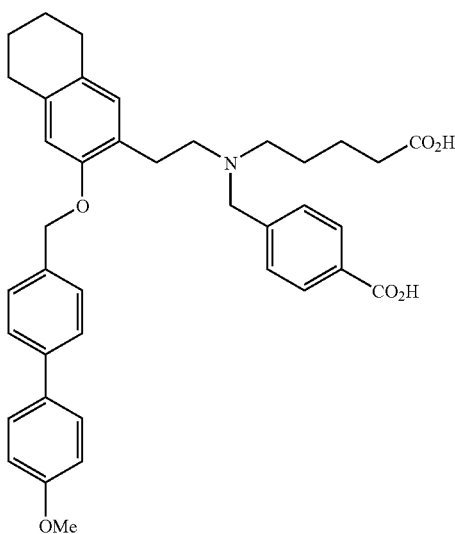

8 ml of a 2-molar aqueous sodium hydroxide solution are added to a solution of 140 mg (0.22 mmol) of methyl 4-{[(2-{3-[(4'-methoxy-1,1'-biphenyl-4-yl)-methoxy]-5,6,7,8-tetrahydro-2-naphthyl}ethyl)(5-methoxy-5-oxopentyl)amino]methyl}benzoate in 4 ml of tetrahydrofuran and 4 ml of methanol, and the mixture is heated at reflux. After the reaction has ended, the mixture is diluted with a little water and extracted with ether. The aqueous phase is adjusted to pH 5 using 2-molar hydrochloric acid and extracted with ethyl acetate. The ethyl acetate extract is evaporated to dryness. The residue is boiled with ether and, after cooling, filtered.

This gives 85 mg (63% yield) of a light-beige solid. Melting point: >240° C. $R_f$ (ethyl acetate): <0.05. $^1$H-NMR (400 MHz, DMSO-$d_6$, δ/ppm): 1.39-1.47 (m, 4H), 1.67-1.70 (m, 4H), 2.11 (t, 2H), 2.44 (m, 2H), 2.57 (m, 4H), 2.65 (m, 4H), 3.62 (s broad, 2H), 3.80 (s, 3H), 5.00 (s, 2H), 6.69 (s, 1H), 6.78 (s, 1H), 7.01 (d, 2H), 7.37 (d, 2H), 7.41 (d, 2), 7.58 (2 d, 4H), 7.83 (d, 2H), 12.38 (broad, 2H). MS (ESI): 622 (M+H$^+$).

Example 14

4-({(4-Carboxybutyl)[2-(3-{[4'-trifluoromethyl)-1,1'-biphenyl-4-yl]methoxy}-5,6,7,8-tetrahydro-2-naphthyl)ethyl]amino}methyl)benzoic acid

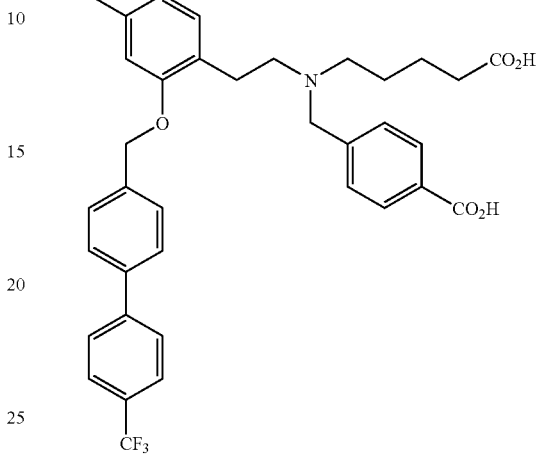

Analogously to the procedure described in Synthesis Example 13, 140 mg of methyl 4-({(5-methoxy-5-oxopentyl)[2-(3-{[4'-(trifluoromethyl)-1,1'-biphenyl-4-yl]-methoxy}-5,6,7,8-tetrahydro-2-naphthyl)ethyl]amino}methyl)benzoate give 79 mg (56% yield) of a white solid.

$^1$H-NMR (300 MHz, DMSO-$d_6$, δ/ppm): 1.42 (m, 4H), 1.68 (m, 4H), 2.10 (dd, 2H), 2.42 (dd, 2H), 2.59 (m, 4H) 2.68 (m, 4H), 3.61 (s, 2H), 5.02 (s, 2H), 6.69 (s, 1H), 6.78 (s, 1H), 7.33 (d, 2H), 7.49 (d, 2H), 7.71 (d, 2H), 7.78-7.88 (m, 6H), 12.27 (broad, 2H). MS (ESI): 660 (M+H$^+$).

Example 15

Methyl 4-({(5-ethoxy-5-oxopentyl)[2-(6-methyl-3-{[4'-(trifluoromethyl)-1,1'-biphenyl-4-yl]methoxy}-2-pyridinyl)ethyl]amino}methyl)benzoate

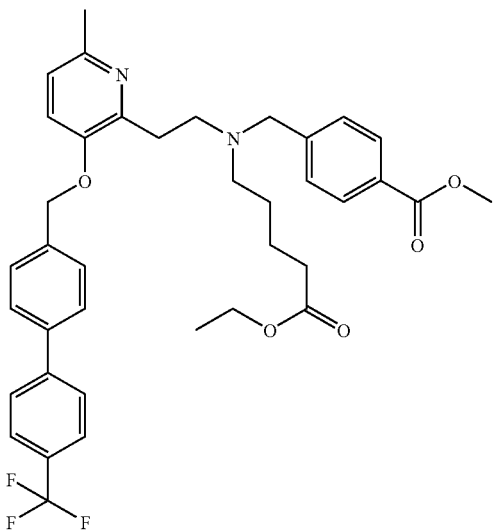

134 mg (0.22 mmol) of methyl 4-{[(2-{3-[(4-bromobenzyl)oxy]-6-methyl-2-pyridinyl}ethyl)(5-ethoxy-5-oxopentyl)amino]methyl}benzoate are dissolved in 2 ml of 1,2-dimethoxyethane, and 51 mg (0.27 mmol) of 4-trifluoromethylphenylboronic acid, 8 mg (0.01 mmol) of bis(triphenylphoshine)palladium(II) chloride and 250 µl of a 2-molar solution of $Na_2CO_3$ in water are added under argon. The reaction mixture is then stirred under reflux for 12 h. The mixture is then cooled and filtered through 3 g of Extrelute, the filter cake is washed with dichloromethane and the filtrate is concentrated using a rotary evaporator. The resulting product is purified by column chromatography (dichloromethane/methanol, 100:5). This gives 135 mg (0.20 mmol, 91% yield) of a colorless oil.

$R_f$ (cyclohexane/ethyl acetate 2:1): 0.28. $^1$H-NMR (200 MHz, DMSO-$d_6$, δ/ppm): 7.92-7.42 (10H, m), 7.39-7.23 (3H, m), 7.01 (1H, d), 5.11 (2H, s), 3.98 (2H, q), 3.59 (2H, s), 3.32 (3H, s), 2.99-2.81 (2H, m), 2.79-2.62 (2H, m), 2.39 (2H, t), 2.33 (3H, s), 2.09 (2H, t), 1.48-1.21 (4H, m), 1.1 (3H, t). MS (ESI): 663 (M+H$^+$).

Example 16

4-({(4-Carboxybutyl)[2-(6-methyl-3-{[4'-trifluoromethyl)-1,1'-biphenyl-4-yl]methoxy}-2-pyridinyl)ethyl]amino}methyl)benzoic acid

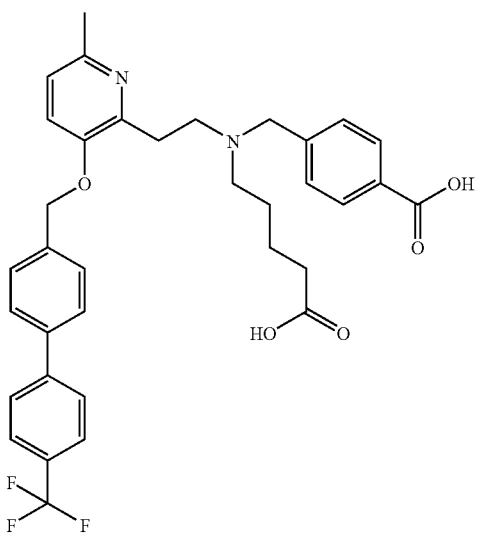

51 µl of a 45% strength solution of NaOH in water are added to a solution of 125 mg (0.19 mmol) of methyl 4-({(5-ethoxy-5-oxopentyl)[2-(6-methyl-3-{[4'-(trifluoromethyl)-1,1'-biphenyl-4-yl]methoxy}-2-pyridinyl)ethyl]amino}methyl)benzoate in 1.0 ml of dioxane and 1 ml of water, and the mixture is stirred at 60° C. for 4 hours. After cooling, the dioxane is removed under reduced pressure and the aqueous phase is adjusted to pH 4-5 using 1-molar hydrochloric acid. This causes the precipitation of the product, which is filtered off, washed with water and dried. This gives 83 mg (0.13 mmol, 89% yield) of a white solid.

$^1$H-NMR (300 MHz, DMSO-$d_6$, δ/ppm): 12.4 (2H, broad), 7.93-7.78 (4H, m), 7.72 (2H, d), 7.68-7.46 (6H, m), 7.33 (1H, d), 7.03 (1H, s), 5.13 (2H, s), 3.75-3.52 (2H, s, broad), 3.04-2.88 (2H, m), 2.87-2.66 (2H, m), 2.57-2.49 (2H, m, partially obscured by DMSO), 2.32 (3H, s), 2.11 (2H, t), 1.51-1.29 (4H, m). MS (ESI): 621 (M+H$^+$).

The invention claimed is:

1. A compound of the formula (I)

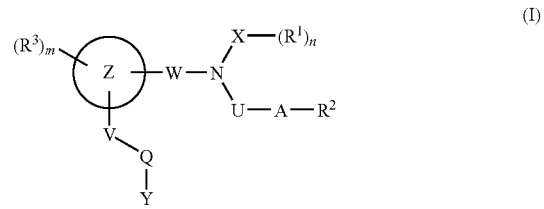

where
Z represents

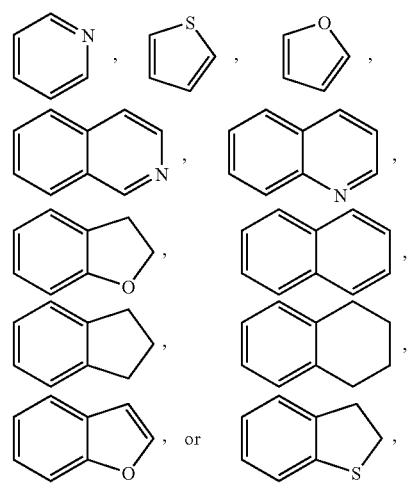

V is missing or represents O, NR$^4$, NR$^4$CONR$^4$, NR$^4$CO, NR$^4$SO$^2$, COO, CONR$^4$ or S(O)$_o$,
where
R$^4$ independently of any other radical R$^4$ optionally present represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o represents 0, 1 or 2,
Q is missing or represents straight-chain or branched alkylene, straight-chain or branched alkenediyl or straight-chain or branched alkynediyl having in each case up to 12 carbon atoms, which radicals may in each case comprise one or more groups selected from the group consisting of O, S(O)$_p$, NR$^5$, CO, NR$^5$SO$_2$ or CONR$^5$ and which may be mono- or polysubstituted by halogen, hydroxyl or alkoxy having up to 4 carbon atoms, where optionally any two atoms of the above chain may be attached to one another forming a three- to eight-membered ring, wherein said three- to eight-membered ring does not consist of O, S(O)$_p$, NR$^5$, or NR$^5$SO$_2$, and
where
R$_5$ represents hydrogen, straight-chain or branched alkyl having up to 8 carbon atoms or cycloalkyl having 3 to 8 carbon atoms which may be substituted by halogen or alkoxy having up to 4 carbon atoms,
p represents 0, 1 or 2, Y represents hydrogen, $NR^8R^9$, aryl having 6 to 10 carbon atoms, or straight-chain or branched cycloalkyl having 3 to 8 carbon atoms,
- where the cyclic radicals may in each case be mono- to trisubstituted by straight-chain or branched alkyl, straight-chain or branched alkenyl, straight-chain or branched alkynyl, straight-chain or branched alkoxy, straight-chain or branched haloalkyl, straight-chain or branched haloalkoxy having in each case up to 8 carbon atoms, straight-chain or branched cycloalkyl having 3 to 8 carbon atoms, halogen, hydroxyl, CN, $SR^6$, $NO_2$, $NR^8R^9$, $NR^7COR^{10}$, $NR^7CONR^7R^{10}$ or $CONR^{11}R^{12}$,
  - where
    - $R^6$ represents hydrogen, straight-chain or branched alkyl having up to 8 carbon atoms, straight-chain or branched haloalkyl having up to 8 carbon atoms or cycloalkyl having 3 to 8 carbon atoms,
    - $R^7$ independently of any other radical $R^7$ optionally present represents hydrogen, straight-chain or branched alkyl having up to 8 carbon atoms or cycloalkyl having 3 to 8 carbon atoms,
    - $R^8$, $R^9$, $R^{11}$ and $R^{12}$ independently of one another represent hydrogen, straight-chain or branched alkyl, straight-chain or branched alkenyl having up to 8 carbon atoms, aryl having 6 to 10 carbon atoms, arylalkyl having 8 to 18 carbon atoms, cycloalkyl having 3 to 8 carbon atoms or a radical of the formula $SO_2R^{13}$, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms,
      - or two substituents selected from $R^8$ and $R^9$ or $R^{11}$ and $R^{12}$ may be attached to one another forming a five- or six-membered ring,
      - where
        - $R^{13}$ represents straight-chain or branched alkyl having up to 4 carbon atoms or aryl having 6 to 10 carbon atoms,
          - where the aryl radical for its part may be mono- or polysubstituted by halogen, CN, $NO_2$, alkyl, alkoxy, haloalkyl or haloalkoxy having up to 6 carbon atoms,
    - $R^{10}$ represents hydrogen, straight-chain or branched alkyl having up to 12 carbon atoms, straight-chain or branched alkenyl having up to 12 carbon atoms, aryl having 6 to 10 carbon atoms, or cycloalkyl having 3 to 8 carbon atoms, which may optionally furthermore be substituted by halogen, hydroxyl, CN, $NO_2$, $NH_2$, $NHCOR^7$, alkyl, alkoxy, haloalkyl or haloalkoxy having up to 6 carbon atoms;
    - and/or the cyclic radicals may in each case be mono- to trisubstituted by aryl having 6 to 10 carbon atoms, a saturated carbocycle having 6 to 10 carbon atoms,
  - which may be attached directly or via a group selected from the group consisting of O, S, SO, $SO_2$, $NR^7$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched haloalkyl, straight-chain or branched haloalkoxy, carbonylalkyl or straight-chain or branched alkenyl having in each case up to 6 carbon atoms, halogen, $SR^6$, CN, $NO_2$, $NR^8R^9$, $CONR^{15}R^{16}$ or $NR^{14}COR^{17}$,
    - where
      - $R^{14}$ represents hydrogen, straight-chain or branched alkyl having up to 8 carbon atoms or cycloalkyl having 3 to 8 carbon atoms,
      - $R^{15}$, $R^{16}$ independently of one another represent hydrogen, straight-chain or branched alkyl having up to 8 carbon atoms, cycloalkyl having 3 to 8 carbon atoms, aryl having 6 to 10 carbon atoms or a radical of the formula $SO_2R^{18}$, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms,
        - where
          - $R^{18}$ represents straight-chain or branched alkyl having up to 4 carbon atoms or aryl having 6 to 10 carbon atoms, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms,
      - and
      - $R^{17}$ represents hydrogen, straight-chain or branched alkyl having up to 12 carbon atoms, straight-chain or branched alkenyl having up to 12 carbon atoms, aryl having 6 to 10 carbon atoms, or cycloalkyl having 3 to 8 carbon atoms, which may optionally furthermore be substituted by halogen, hydroxyl, CN, $NO_2$, $NH_2$, $NHCOR^7$, alkyl, alkoxy, haloalkyl or haloalkoxy having up to 6 carbon atoms;
      - and/or the cyclic radicals may be fused with an aromatic or saturated carbocycle having 1 to 10 carbon atoms,
- $R^3$ represents hydrogen, halogen, straight-chain or branched alkyl which may optionally carry one or more substituents from the group consisting of C1-6-alkoxy, $NR^{19}R^{20}$ and cycloalkyl having 3 to 8 carbon atoms, straight-chain or branched haloalkyl, straight-chain or branched alkoxy, or alkoxycarbonyl having in each case up to 4 carbon atoms, CN, $NO_2$, $NR^{19}R^{20}$, $SR^{17}$, $SO_2R^{17}$, cycloalkyl having 3 to 8 carbon atoms, haloalkoxy, haloalkoxy having up to 6 carbon atoms, cycloalkoxy having up to 14 carbon atoms, $CONH_2$, $CONR^{17}R^{17}$, $SO_2NH_2$, $SO_2NR^{17}R^{17}$, alkoxyalkoxy having up to 12 carbon atoms, $NHCOOR^{17}$, $NHCOR^{17}$, $NHSO_2R^{17}$, $NHCONH_2$, $OCONR^{17}R^{17}$, $OSO_2R^{17}$, $C_{2-12}$-alkenyl or $C_{2-12}$-alkynyl,
  - where
    - $R^{19}$ and $R^{20}$ independently of one another represent hydrogen, straight-chain or branched alkyl having up to 4 carbon atoms or cycloalkyl having 3 to 8 carbon atoms,
- m represents an integer from 1 to 4,
- W represents straight-chain or branched alkylene having up to 6 carbon atoms or straight-chain or branched alkenediyl having up to 6 carbon atoms which may in each case contain a group selected from the group consisting of O, $S(O)_q$, $NR^{21}$, CO or $CONR^{21}$, or represents CO, NHCO or OCO,
  - where
    - q represents 0, 1 or 2,
    - $R^{21}$ represents hydrogen, straight-chain or branched alkyl having up to 8 carbon atoms or cycloalkyl having 3 to 8 carbon atoms, U represents straight-chain or branched alkyl having up to 4 carbon atoms, A represents aryl having 6 to 10 carbon atoms,
which may optionally be mono- to trisubstituted by halogen, straight-chain or branched alkyl, straight-chain or branched haloalkyl, straight-chain or branched alkoxy, haloalkoxy or alkoxycarbonyl having up to 4 carbon atoms, CN, NO$_2$ or NR$^{22}$R$^{23}$,
where
R$^{22}$ and R$^{23}$ in each case independently of one another represent hydrogen, straight-chain or branched alkyl having up to 8 carbon atoms or cycloalkyl having 3 to 8 carbon atoms, carbonylalkyl or sulfonylalkyl, R$^2$ represents tetrazolyl, COOR$^{24}$ or CONR$^{25}$R$^{26}$,
where
R$^{24}$ represents hydrogen, alkyl having 1 to 8 carbon atoms or cycloalkyl having 3 to 8 carbon atoms R$^{25}$ and R$^{26}$ in each case independently of one another represent hydrogen, straight-chain or branched alkyl having up to 8 carbon atoms, cycloalkyl having 3 to 8 carbon atoms or a radical of the formula SO$_2$R$^{27}$,
or
R$^{25}$ and R$^{26}$ together form a five- or six-membered ring,
where
R$^{27}$ represents straight-chain or branched alkyl having up to 4 carbon atoms or aryl having 6 to 10 carbon atoms,
where the aryl radical for its part may be mono- or polysubstituted by halogen, CN, NO$_2$, alkyl, alkoxy, haloalkyl or haloalkoxy having up to 6 carbon atoms, X represents straight-chain or branched alkylene having up to 12 carbon atoms or straight-chain or branched alkenediyl having up to 12 carbon atoms, which may in each case contain one to three groups selected from the group consisting of O, S(O)$_r$, NR$^{28}$, CO or CONR$^{29}$, aryl and aryloxy having 6 to 10 carbon atoms, where the aryl radical for its part may be mono- or polysubstituted by halogen, CN, NO$_2$, alkyl, alkoxy, haloalkyl or haloalkoxy having up to 6 carbon atoms, where optionally any two atoms of the abovementioned chains are attached to one another via an alkyl chain forming a three- to eight-membered ring, wherein said three- to eight-membered ring does not consist of O, S(O)$_p$, or NR$^{28}$, and,
where
r represents 0, 1 or 2,
R$^{28}$ represents hydrogen, alkyl having 1 to 8 carbon atoms or cycloalkyl having 3 to 8 carbon atoms,
R$^{29}$ represents hydrogen, straight-chain or branched alkyl having up to 8 carbon atoms or cycloalkyl having 3 to 8 carbon atoms,
n represents 1 or 2;

R$^1$ represents, COOR$^{30}$ or CONR$^{31}$R$^{32}$,
where
R$^{30}$ represents hydrogen, alkyl having 1 to 8 carbon atoms or cycloalkyl having 3 to 8 carbon atoms
R$^{31}$ and R$^{32}$ in each case independently of one another represent hydrogen, straight-chain or branched alkyl having up to 8 carbon atoms, cycloalkyl having 3 to 8 carbon atoms or a radical of the formula SO$_2$R$^{33}$,
where
R$^{33}$ represents straight-chain or branched alkyl having up to 4 carbon atoms or aryl having 6 to 10 carbon atoms,
where the aryl radical for its part may be mono- or polysubstituted by halogen, CN, NO$_2$, alkyl, alkoxy, haloalkyl or haloalkoxy having up to 6 carbon atoms, or a stereoisomer or a salt thereof.

2. A compound as claimed in claim 1,
where
Z represents a cyclic radical from the group consisting of

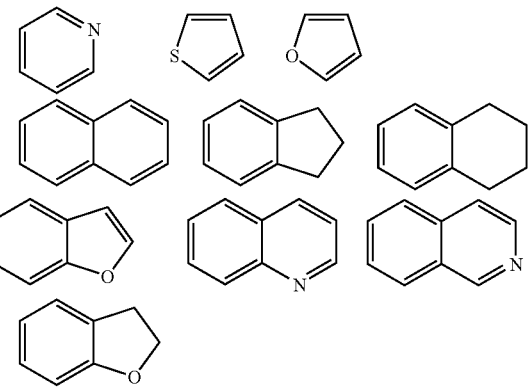

where the radicals V and W may be attached to any carbon ring atom or any nitrogen ring atom optionally present, selected;

V is missing or represents O, NR$^4$, NR$^4$CONR$^4$, NR$^4$CO, NR$^4$SO$_2$, COO, CONR$^4$ or S(O)$_o$,
where
R$^4$ independently of any other radical R$^4$ optionally present represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o represents 0, 1 or 2, Q is missing or represents straight-chain or branched alkylene, straight-chain or branched alkenediyl or straight-chain or branched alkynediyl having in each case up to 12 carbon atoms, which radicals may in each case comprise one or more groups selected from the group consisting of O, S(O)$_p$, NR$^5$, CO, NR$^5$SO$_2$ or CONR$^5$ and which may be mono- or polysubstituted by halogen, hydroxyl or alkoxy having up to 4 carbon atoms, where optionally any two atoms of the above chain may be attached to one another forming a three- to eight-membered ring, wherein said three- to eight-membered ring does not consist of O, S(O)$_p$, NR$^5$, or NR$^5$SO$_2$, and
where
R$_5$ represents hydrogen, straight-chain or branched alkyl having up to 8 carbon atoms or cycloalkyl having 3 to 8 carbon atoms which may be substituted by halogen or alkoxy having up to 4 carbon atoms,
p represents 0, 1 or 2, Y represents hydrogen, NR$^8$R$^9$, aryl having 6 to 10 carbon atoms, or branched cycloalkyl having 3 to 8 carbon atoms, which may also be attached via N,
where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 8 carbon atoms, straight-chain or branched cycloalkyl having 3 to 8 carbon atoms, halogen, hydroxyl, CN, $SR^6$, $NO_2$, $NR^8R^9$, $NR^7COR^{10}$, $NR^7CONR^7R^{10}$ or $CONR^{11}R^{12}$, where $R^6$ represents hydrogen, straight-chain or branched alkyl having up to 8 carbon atoms, straight-chain or branched haloalkyl having up to 8 carbon atoms or cycloalkyl having 3 to 8 carbon atoms, $R^7$ independently of any other radical $R^7$ optionally present represents hydrogen, straight-chain or branched alkyl having up to 8 carbon atoms or cycloalkyl having 3 to 8 carbon atoms, $R^8$, $R^9$, $R^{11}$ and $R^{12}$ independently of one another represent hydrogen, straight-chain or branched alkyl, straight-chain or branched alkenyl having up to 8 carbon atoms, aryl having 6 to 10 carbon atoms, arylalkyl having 8 to 18 carbon atoms, cycloalkyl having 3 to 8 carbon atoms or a radical of the formula $SO_2R^{13}$, where the aryl radical for its part may be mono- or polysubstituted by halogen, hydroxyl, CN, $NO_2$, $NH_2$, $NHCOR^7$, alkyl, alkoxy, haloalkyl or haloalkoxy having up to 6 carbon atoms, or two substituents selected from $R^8$ and $R^9$ or $R^{11}$ and $R^{12}$ may be attached to one another forming a five- or six-membered ring, where $R^{13}$ represents straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, haloalkyl or haloalkoxy having up to 6 carbon atoms, $R^{10}$ represents hydrogen, straight-chain or branched alkyl having up to 12 carbon atoms, straight-chain or branched alkenyl having up to 12 carbon atoms, aryl having 6 to 10 carbon atoms, or cycloalkyl having 3 to 8 carbon atoms, which may optionally furthermore be substituted by halogen, hydroxyl, CN, $NO_2$, $NH_2$, $NHCOR^7$, alkyl, alkoxy, haloalkyl or haloalkoxy having up to 6 carbon atoms;

and/or the cyclic radicals may in each case be mono- to trisubstituted by aryl having 6 to 10 carbon atoms, which may be attached directly or via a group selected from the group consisting of O, S, SO, $SO_2$, $NR^7$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched haloalkyl, straight-chain or branched haloalkoxy, carbonylalkyl or straight-chain or branched alkenyl having in each case up to 6 carbon atoms, halogen, $SR^6$, CN, $NO_2$, $NR^8R^9$, $CONR^{15}R^{16}$ or $NR^{14}COR^{17}$, where $R^{14}$ represents hydrogen, straight-chain or branched alkyl having up to 8 carbon atoms or cycloalkyl having 3 to 8 carbon atoms, $R^{15}$, $R^{16}$ independently of one another represent hydrogen, straight-chain or branched alkyl having up to 8 carbon atoms, cycloalkyl having 3 to 8 carbon atoms or a radical of the formula $SO_2R^{18}$, where $R^{18}$ represents straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, haloalkyl or haloalkoxy having up to 6 carbon atoms, and $R^{17}$ represents hydrogen, straight-chain or branched alkyl having up to 12 carbon atoms, straight-chain or branched alkenyl having up to 12 carbon atoms, aryl having 6 to 10 carbon atoms, or cycloalkyl having 3 to 8 carbon atoms, which may optionally furthermore be substituted by halogen, CN, $NO_2$, alkyl, alkoxy, haloalkyl or haloalkoxy having up to 6 carbon atoms;

and/or the cyclic radicals may be fused with an aromatic or saturated carbocycle having 1 to 10 carbon atoms, $R^3$ represents hydrogen, halogen, straight-chain or branched alkyl which may optionally carry one or more substituents from the group consisting of C1-6-alkoxy, $NR^{19}R^{20}$ and cycloalkyl having 3 to 8 carbon atoms, straight-chain or branched haloalkyl, straight-chain or branched alkoxy, or alkoxycarbonyl having in each case up to 4 carbon atoms, CN, $NO_2$, $NR^{19}R^{20}$, $SR^{17}$, $SO_2R^{17}$, cycloalkyl having 3 to 8 carbon atoms, haloalkoxy, haloalkoxy having up to 6 carbon atoms, cycloalkoxy having up to 14 carbon atoms, $CONH_2$, $CONR^{17}R^{17}$, $SO_2NH_2$, $SO_2NR^{17}R^{17}$, alkoxyalkoxy having up to 12 carbon atoms, $NHCOOR^{17}$, $NHCOR^{17}$, $NHSO_2R^{17}$, $NHCONH_2$, $OCONR^{17}R^{17}$, $C_{2-12}$-alkenyl or $C_{2-12}$-alkynyl, m represents an integer from 1 to 4, W represents straight-chain or branched alkylene or straight-chain or branched alkenediyl having in each case up to 4 carbon atoms, U represents —$CH_2$—, A represents phenyl which may optionally be mono- to trisubstituted by halogen, straight-chain or branched alkyl, straight-chain or branched haloalkyl or straight-chain or branched alkoxy having up to 4 carbon atoms, $R^2$ represents $COOR^{24}$, where $R^{24}$ represents hydrogen or straight-chain or branched alkyl having up to 6 carbon atoms, X represents straight-chain or branched alkylene having up to 8 carbon atoms or straight-chain or branched alkenediyl having up to 8 carbon atoms which may in each case contain one to three groups selected from the group consisting of phenyl, phenyloxy, O, CO and $CONR^{29}$, where $R^{29}$ represents hydrogen, straight-chain or branched alkyl having up to 6 carbon atoms or cycloalkyl having 3 to 6 carbon atoms, n represents 1 or 2;

$R^1$ represents $COOR^{30}$, where $R^{30}$ represents hydrogen or straight-chain or branched alkyl having up to 6 carbon atoms.

3. A compound as claimed in claim 1, where

Z represents a cyclic radical from the group consisting of

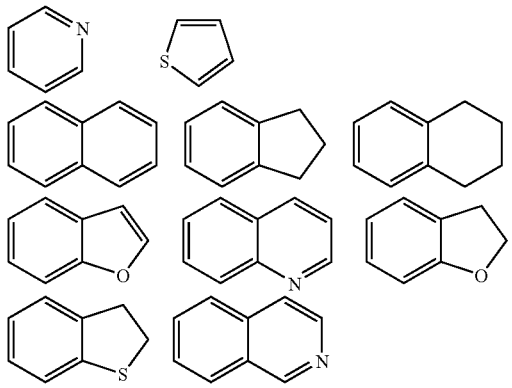

where the radicals V and W may be attached to any carbon ring atom or any nitrogen ring atom optionally present, selected;

V is missing or represents O, S or $NR^4$,
where
$R^4$ represents hydrogen or methyl, Q is missing or represents straight-chain or branched alkylene having up to 9 carbon atoms or straight-chain or branched alkenediyl or straight-chain or branched alkynediyl having up to 4 carbon atoms which may be monosubstituted by halogen, Y represents H, $NR^8R^9$, cyclohexyl, phenyl, naphtyl where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$,
where
$R^6$ represents hydrogen, straight-chain or branched alkyl having up to 8 carbon atoms, or straight-chain or branched haloalkyl having up to 4 carbon atoms,
$R^7$ represents hydrogen, or straight-chain or branched alkyl having up to 4 carbon atoms,
$R^8$, $R^9$, $R^{11}$ and $R^{12}$ independently of one another represent hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN,
or two substituents selected from $R^8$ and $R^9$ or $R^{11}$ and $R^{12}$ may be attached to one another forming a five- or six-membered ring
$R^{10}$ represents hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;
and/or the cyclic radicals may in each case be mono- to trisubstituted by phenyl
which may be attached directly or via a group selected from the group consisting of O, S, SO, $SO_2$, $NR^4$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched haloalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$,
where
$R^{14}$ represents hydrogen, straight-chain or branched alkyl having up to 8 carbon atoms or cycloalkyl having 3 to 8 carbon atoms,
and
$R^{17}$ represents hydrogen, straight-chain or branched alkyl having up to 12 carbon atoms, straight-chain or branched alkenyl having up to 12 carbon atoms, aryl having 6 to 10 carbon atoms, or cycloalkyl having 3 to 8 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;
and/or the cyclic radicals may be fused with an aromatic or saturated carbocycle having I to 10 carbon,
$R^3$ represents hydrogen, methyl or fluorine,
m represents an integer from 1 to 2,
W represents $CH_2$, —$CH_2CH_2$—, $CH_2CH_2CH_2$, $CH=CHCH_2$,
U represents —$CH_2$—,
A represents phenyl, pyridyl, which may optionally be mono- to trisubstituted by methyl, ethyl, n-propyl, i-propyl, n-butyl, i-butyl, s-butyl, t-butyl, $CF_3$, methoxy, ethoxy, F, Cl, Br,
$R^2$ represents $COOR^{24}$,
where
$R^{24}$ represents hydrogen or straight-chain or branched alkyl having up to 4 carbon atoms,
X represents straight-chain or branched alkylene having up to 8 carbon atoms or straight-chain or branched alkenediyl having up to 8 carbon atoms which may in each case contain one to three groups from the group consisting of phenyl, phenyloxy, O, CO and $CONR^{30}$,
where
$R^{30}$ represents-hydrogen, straight-chain or branched alkyl having up to 6 carbon atoms or cycloalkyl having 3 to 6 carbon atoms,
n represents 1 or 2;
$R^1$ represents $COOR^{35}$,
where
$R^{35}$ represents hydrogen or straight-chain or branched alkyl having up to 6 carbon atoms.

4. A compound as claimed in claim 1,
where
Z represents a cyclic radical from the group consisting of

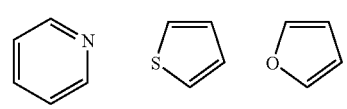

-continued where the radicals V and W may be attached to any carbon ring atom or any nitrogen ring atom optionally present, selected;

V represents O,

Q represents straight-chain or branched alkylene having up to 9 carbon atoms or straight-chain or branched alkenediyl or straight-chain or branched alkynediyl having up to 4 carbon atoms which may be monosubstituted by halogen, Y represents H, cyclohexyl, or phenyl where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$, where $R^6$ represents hydrogen, straight-chain or branched alkyl having up to 4 carbon atoms, or straight-chain or branched haloalkyl having up to 4 carbon atoms, $R^7$ represents hydrogen, or straight-chain or branched alkyl having up to 4 carbon atoms, $R^8$, $R^9$, $R^{11}$ and $R^{12}$ independently of one another represent hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents selected from $R^8$ and $R^9$ or $R^{11}$ and $R^{12}$ may be attached to one another forming a five- or six-membered ring which may be interrupted by O or N, $R^{10}$ represents hydrogen, straight-chain or branched alkyl having up to 4 carbon atoms, or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl which may be attached directly or via a group selected from the group consisting of O, S, SO, $SO_2$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched haloalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$, where $R^{14}$ represents hydrogen, straight-chain or branched alkyl having up to 6 carbon atoms or cycloalkyl having 3 to 6 carbon atoms, and $R^{17}$ represents hydrogen, straight-chain or branched alkyl having up to 6 carbon atoms, straight-chain or branched alkenyl having up to 6 carbon atoms, aryl having 6 to 10 carbon atoms, or cycloalkyl having 3 to 6 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon $R^3$ represents hydrogen, methyl or fluorine, m represents an integer from 1 to 2, W represents —$CH_2$— or —$CH_2CH_2$—, U represents —$CH_2$—, A represents phenyl which may optionally be mono- to trisubstituted by methyl, ethyl, n-propyl, i-propyl, n-butyl, i-butyl, s-butyl, t-butyl, $CF_3$, methoxy, ethoxy, F, Cl, Br, $R^2$ represents $COOR^{24}$, where $R^{24}$ represents hydrogen or straight-chain or branched alkyl having up to 4 carbon atoms, X represents straight-chain or branched alkylene having up to 6 carbon atoms or straight-chain or branched alkenediyl having up to 6 carbon atoms which may in each case contain one to three groups selected from the group consisting of phenyloxy, O, CO and $CONR^{30}$, where $R^{30}$ represents hydrogen, straight-chain or branched alkyl having up to 6 carbon atoms or cycloalkyl having 3 to 6 carbon atoms, n represents 1 or 2;

$R^1$ represents $COOR^{35}$, where $R^{35}$ represents hydrogen or straight-chain or branched alkyl having up to 4 carbon atoms.

5. A compound as claimed in claim 1, where

Z represents a cyclic radical from the group consisting of where the radicals V and W may be attached to any carbon ring atom or any nitrogen ring atom optionally present, selected;

V represents O,

Q represents straight-chain or branched alkylene having up to 9 carbon atoms or straight-chain or branched alkenediyl or straight-chain or branched alkynediyl having up to 4 carbon atoms which may be monosubstituted by halogen, Y represents H, cyclohexyl, or phenyl or
  where the cyclic radicals may in each case be mono- to trisubstituted by straight-chain or branched alkyl, straight-chain or branched alkenyl, straight-chain or branched alkynyl, straight-chain or branched alkoxy, straight-chain or branched alkoxyalkoxy, straight-chain or branched haloalkyl, straight-chain or branched haloalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$,
    where
    $R^6$ represents hydrogen, straight-chain or branched alkyl having up to 4 carbon atoms, or straight-chain or branched haloalkyl having up to 4 carbon atoms,
    $R^7$ represents hydrogen, or straight-chain or branched alkyl having up to 4 carbon atoms,
    $R^8$, $R^9$, $R^{11}$ and $R^{12}$ independently of one another represent hydrogen, straight-chain or branched alkyl having up to 4 carbon atoms, or phenyl,
      where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN,
    or two substituents selected from $R^8$ and $R^9$ or $R^{11}$ and $R^{12}$ may be attached to one another forming a five- or six-membered ring which may be interrupted by O or N,
    $R^{10}$ represents hydrogen, straight-chain or branched alkyl having up to 4 carbon atoms, or phenyl,
      where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;
  and/or the cyclic radicals may in each case be mono- to trisubstituted by phenyl
    which may be attached directly or via a group selected from the group consisting of O, S, SO, $SO_2$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched haloalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$,
    where
    $R^{14}$ represents hydrogen, straight-chain or branched alkyl having up to 6 carbon atoms or cycloalkyl having 3 to 6 carbon atoms,
    and
    $R^{17}$ represents hydrogen, straight-chain or branched alkyl having up to 6 carbon atoms, straight-chain or branched alkenyl having up to 6 carbon atoms, aryl having 6 to 10 carbon atoms, or cycloalkyl having 3 to 6 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;
  and/or the cyclic radicals may be fused with an aromatic or saturated carbocycle having 1 to 10 carbon atoms, $R^3$ represents hydrogen, methyl or fluorine, m represents an integer from 1 to 2, W represents —$CH_2$— or —$CH_2CH_2$—, U represents —$CH_2$—, A represents phenyl which may optionally be mono- to trisubstituted by methyl, ethyl, n-propyl, i-propyl, n-butyl, i-butyl, s-butyl, t-butyl, $CF_3$, methoxy, ethoxy, F, Cl, Br, $R^2$ represents COOH, X represents straight-chain or branched alkylene having up to 6 carbon atoms or straight-chain or branched alkenediyl having up to 6 carbon atoms which may in each case contain one to three groups selected from the group consisting of phenyloxy, O, CO and $CONR^{30}$,
  where
  $R^{30}$ represents hydrogen, straight-chain or branched alkyl having up to 6 carbon atoms or cycloalkyl having 3 to 6 carbon atoms, n represents 1 or 2;

$R^1$ represents COOH.

6. A compound as claimed in claim 1,
where
Z represents a cyclic radical from the group consisting of where the radicals V and W may be attached to any carbon ring atom or any nitrogen ring atom optionally present, selected;

V represents O,

Q represents CH$_2$,
Y represents phenyl which is substituted by a radical selected from the group consisting of 2-phenylethyl, cyclohexyl, 4-chlorophenyl, 4-methoxyphenyl, 4-trifluoromethylphenyl, 4-cyanophenyl, 4-chlorophenoxy, 4-methoxyphenoxy, 4-trifluoromethylphenoxy, 4-cyanophenoxy, 4-methylphenyl,
R$^3$ represents hydrogen, methyl or fluorine,
m represents an integer from 1 to 2,
W represents —CH$_2$CH$_2$—,
U represents —CH$_2$—,
A represents phenyl,
R$^2$ represents COOH, where R$^2$ is located in the 4-position to the radical U,
X represents (CH$_2$)$_4$,
R$^1$ represents COOH.

7. A compound as claimed in claim 1, where
Z represents a cyclic radical from the group consisting of

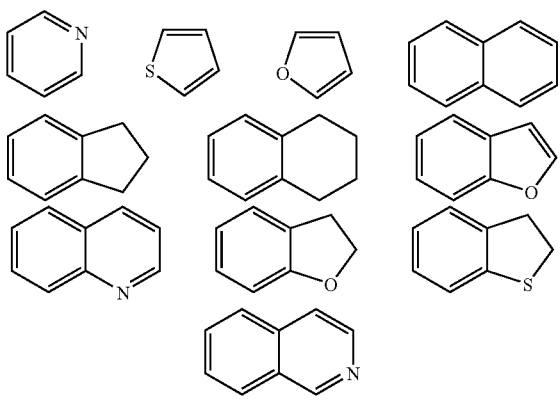

where the radicals V and W may be attached to any carbon ring atom or any nitrogen ring atom optionally present, selected;
V is missing,
Q represents CH$_2$O which is attached via its carbon atom to Z,
Y represents phenyl which is substituted by a radical selected from the group consisting of 2-phenylethyl, cyclohexyl, 4-chlorophenyl, 4-methoxyphenyl, 4-trifluoromethylphenyl, 4-cyanophenyl, 4-chlorophenoxy, 4-methoxyphenoxy, 4-trifluoromethylphenoxy, 4-cyanophenoxy, 4-methylphenyl, 4-tert-butyiphenyl, 4-carboxyphenyl, 4-fluorophenyl, 3-methoxyphenyl, 2,4-dichlorophenyl,
R$^3$ represents hydrogen, methyl or fluorine,
m represents an integer from 1 to 2,
W represents —CH$_2$CH$_2$—,
U represents —CH$_2$—,
A represents phenyl,
R$^2$ represents COOH where R$^2$ is located in the 4-position to the radical U,
X represents (CH$_2$)$_4$,
R$^1$ represents COOH.

8. A pharmaceutical composition comprising at least one compound of the general formula (I) as claimed in claim 1.

9. A method of treating a cardiovascular disorder selected from high blood pressure, heart failure, stable and unstable angina pectoris or arrhythmias, a thromboembolic disorder selected from myocardial infarction, stroke, transitory and ischemic attacks, percutaneous transluminal angioplasties, or percutaneous transluminal coronary angioplasties, an ischemia, hypertension, arteriosclerosis, a fibrosis of the liver or pulmonary fibrosis, comprising administering to a mammal in need thereof at least one compound of the general formula (I) as claimed in claim 1.

10. The method of claim 9 wherein the fibrotic disorder is fibrosis of the liver.

11. The method of claim 9 wherein the cardiovascular disorder is angina pectoris or heart failure.

* * * * *